United States Patent
Bhavaraju et al.

(10) Patent No.: US 10,145,019 B2
(45) Date of Patent: Dec. 4, 2018

(54) CUSTOM IONIC LIQUID ELECTROLYTES FOR ELECTROLYTIC DECARBOXYLATION

(71) Applicant: FIELD UPGRADING LIMITED, Calgary (CA)

(72) Inventors: Sai Bhavaraju, West Jordan, UT (US); James Mosby, Salt Lake City, UT (US); Patrick McGuire, Salt Lake City, UT (US); Mukund Karanjikar, Sandy, UT (US); Daniel Taggart, Salt Lake City, UT (US); Jacob Staley, West Jordan, UT (US)

(73) Assignee: ENLIGHTEN INNOVATIONS INC., Calgary (CA)

( * ) Notice: Subject to any disclaimer, the term of this patent is extended or adjusted under 35 U.S.C. 154(b) by 0 days.

(21) Appl. No.: 15/290,864

(22) Filed: Oct. 11, 2016

(65) Prior Publication Data

US 2017/0088962 A1    Mar. 30, 2017

Related U.S. Application Data

(60) Division of application No. 14/206,981, filed on Mar. 12, 2014, now Pat. No. 9,493,882, and a
(Continued)

(51) Int. Cl.
  *C25B 3/00* (2006.01)
  *C25B 3/02* (2006.01)
  (Continued)

(52) U.S. Cl.
  CPC .............. *C25B 3/10* (2013.01); *C07C 1/2078* (2013.01); *C07C 29/32* (2013.01); *C07C 51/412* (2013.01); *C10G 3/00* (2013.01); *C25B 3/00* (2013.01); *C25B 9/08* (2013.01); *C25B 15/08* (2013.01); *C10G 2300/1011* (2013.01); *C10G 2300/44* (2013.01); *Y02P 30/20* (2015.11)

(58) Field of Classification Search
  CPC ................................... C25B 3/02; C25B 3/10
  USPC .................................................. 205/440, 442
  See application file for complete search history.

(56) References Cited

U.S. PATENT DOCUMENTS 2,760,926 A * 8/1956 Kronenthal ............... C25B 3/00
                                                       205/455
2,867,569 A    1/1959 Kronenthal
(Continued)

FOREIGN PATENT DOCUMENTS

CN    101089231 A    12/2007
CN    101336313 A    12/2008
(Continued)

OTHER PUBLICATIONS

Matsuda, "Relation Between Kolbe Reaction and Hydrogen-Ion Concentration. II. Electrolysis of Potassium Acetate Solutions in the Presence of Ammonium Carbonate," Nippon Kagaku Kaishi (1921-47) (no month, 1930), vol. 51, pp. 632-634. Abstract Only.*
(Continued)

Primary Examiner — Edna Wong
(74) Attorney, Agent, or Firm — Foley & Lardner LLP

(57) ABSTRACT

Methods, equipment, and reagents for preparing organic compounds using custom electrolytes based on different ionic liquids in electrolytic decarboxylation reactions are disclosed.

24 Claims, 8 Drawing Sheets

Related U.S. Application Data continuation-in-part of application No. 12/092,685, filed on Apr. 22, 2011, now Pat. No. 9,051,656, and a continuation-in-part of application No. 12/840,401, filed on Jul. 21, 2010, now abandoned, and a continuation-in-part of application No. 12/840,913, filed on Jul. 21, 2010, now Pat. No. 8,647,492, and a continuation-in-part of application No. 12/840,508, filed on Jul. 21, 2010, now Pat. No. 8,506,789.

(60) Provisional application No. 61/778,037, filed on Mar. 12, 2013.

(51) Int. Cl.

| | |
|---|---|
| C25B 3/10 | (2006.01) |
| C07C 29/32 | (2006.01) |
| C07C 1/207 | (2006.01) |
| C10G 3/00 | (2006.01) |
| C25B 9/08 | (2006.01) |
| C25B 15/08 | (2006.01) |
| C07C 51/41 | (2006.01) |

(56) References Cited

U.S. PATENT DOCUMENTS

| | | |
|---|---|---|
| 3,193,479 A | 7/1965 | Baizer |
| 3,249,521 A | 5/1966 | Baizer |
| 3,885,626 A | 5/1975 | Gale et al. |
| 3,896,011 A | 7/1975 | Isoya et al. |
| 3,984,295 A | 10/1976 | Kametani et al. |
| 3,992,471 A | 11/1976 | Priegnitz |
| 3,994,471 A | 11/1976 | Turolla |
| 4,006,065 A * | 2/1977 | Meresz ............... C25B 3/10 |
| | | 205/462 |
| 4,093,521 A | 6/1978 | Renton et al. |
| 4,110,191 A | 8/1978 | Specht et al. |
| 4,123,336 A | 10/1978 | Seko et al. |
| 4,182,661 A | 1/1980 | Lynch et al. |
| 4,402,804 A | 9/1983 | Jackson |
| 4,450,059 A | 5/1984 | Eskamani et al. |
| 4,464,236 A | 8/1984 | Noding |
| 5,084,146 A | 1/1992 | Huang |
| 5,290,404 A | 3/1994 | Toomey |
| 5,290,405 A | 3/1994 | Joshi et al. |
| 5,580,430 A | 12/1996 | Balagopal et al. |
| 5,625,059 A | 4/1997 | Sedelmeier et al. |
| 5,633,400 A | 5/1997 | Wagner et al. |
| 5,841,002 A | 11/1998 | Harrison et al. |
| 5,892,107 A | 4/1999 | Farone et al. |
| 6,193,872 B1 | 2/2001 | Reason et al. |
| 6,238,543 B1 | 5/2001 | Law et al. |
| 6,362,380 B1 | 3/2002 | Eicken et al. |
| 6,392,091 B2 | 5/2002 | Tsong-Dar |
| 7,166,724 B2 | 1/2007 | Hilarious et al. |
| 8,506,789 B2 | 8/2013 | Bhavaraju et al. |
| 8,647,492 B2 | 2/2014 | Karanjikar et al. |
| 8,821,710 B2 | 9/2014 | Bhavaraju et al. |
| 8,853,463 B2 | 10/2014 | Karanjikar et al. |
| 2001/0019020 A1 | 9/2001 | Merk et al. |
| 2002/0015883 A1 * | 2/2002 | Hilarius ............... C07F 5/04 |
| | | 429/188 |
| 2003/0024879 A1 | 2/2003 | Carson et al. |
| 2004/0035715 A1 | 2/2004 | Putter et al. |
| 2004/0124094 A1 | 7/2004 | Hakansson et al. |
| 2005/0126926 A1 | 6/2005 | Ogihara et al. |
| 2005/0177008 A1 | 8/2005 | Balagopal et al. |
| 2007/0012578 A1 | 1/2007 | Albers et al. |
| 2007/0074975 A1 | 4/2007 | Buschmann et al. |
| 2007/0138020 A1 | 6/2007 | Balagopal et al. |
| 2007/0181437 A1 | 8/2007 | Stapley et al. |
| 2008/0142373 A1 | 6/2008 | Joshi et al. |
| 2008/0177114 A1 | 7/2008 | Goossen et al. |
| 2008/0245671 A1 | 10/2008 | Balagopal et al. |
| 2009/0057162 A1 | 3/2009 | Balagopal et al. |
| 2009/0074611 A1 | 3/2009 | Monzyk et al. |
| 2009/0107850 A1 | 4/2009 | Fang et al. |
| 2009/0305942 A1 | 12/2009 | Day et al. |
| 2010/0044242 A1 | 2/2010 | Bhavaraju et al. |
| 2010/0159553 A1 | 6/2010 | Bradin |
| 2010/0258447 A1 * | 10/2010 | Fan ............... C25L 33/04 |
| | | 205/413 |
| 2010/0324310 A1 | 12/2010 | Dumesic et al. |
| 2010/0331170 A1 | 12/2010 | Balagopal et al. |
| 2011/0000782 A1 | 1/2011 | Reddy et al. |
| 2011/0024288 A1 * | 2/2011 | Bhavaraju ............... C10G 3/00 |
| | | 204/252 |
| 2011/0027848 A1 | 2/2011 | Karanjikar et al. |
| 2011/0035995 A1 | 2/2011 | Williams |
| 2011/0111475 A1 * | 5/2011 | Kuhry ............... C12N 1/22 |
| | | 435/166 |
| 2011/0168569 A1 | 7/2011 | Bhavaraju et al. |
| 2011/0226633 A1 | 9/2011 | Bhavaraju et al. |
| 2011/0240484 A1 | 10/2011 | Pendleton et al. |
| 2012/0031769 A1 | 2/2012 | Bhavaraju et al. |
| 2012/0035403 A1 | 2/2012 | Flytzani-Stephanopoulos et al. |
| 2012/0103529 A1 | 5/2012 | Binner et al. |
| 2012/0123168 A1 | 5/2012 | Bhavaraju |
| 2012/0142945 A1 | 6/2012 | Hwang et al. |
| 2012/0316093 A1 | 12/2012 | Zhan et al. |
| 2013/0001095 A1 | 1/2013 | Bhavaraju et al. |
| 2013/0186770 A1 | 7/2013 | Mosby et al. |
| 2013/0284607 A1 | 10/2013 | Bhavaraju et al. |
| 2014/0154766 A1 | 6/2014 | Karanjikar et al. |
| 2015/0361565 A1 | 12/2015 | Mosby et al. |

FOREIGN PATENT DOCUMENTS

| | | | |
|---|---|---|---|
| EP | 0838435 | 4/1998 | |
| GB | 787976 | 12/1957 | |
| JP | 06271499 | 9/1994 | |
| SU | 979325 | 12/1982 | |
| WO | WO-2006/077204 A2 | 7/2006 | |
| WO | WO 2007027669 A1 * | 3/2007 | ............... C10L 1/08 |
| WO | 2007/095215 | 8/2007 | |
| WO | WO2011133906 | 10/2011 | |
| WO | WO2012103529 | 8/2012 | |

OTHER PUBLICATIONS

Matsuda, "Relation Between Kolbe's Reaction and Hydrogen-Ion Concentration. III. Comparison of the Electrolysis of Ammonium Acetate and Potassium Acetate," Nippon Kagaku Kaishi (1921-47) (no month, 1931), vol. 52, pp. 249-262. Abstract Only.*

Hibino, et al., "Oxidative Coupling of CH4 using Alkali-Metal Ion Conductors as a Solid Electrolyte", J. Chem. Soc., Faraday Trans. (no month, 1996), vol. 92, No. 13, pp. 2393-2396, Jan. 1, 1996, 2393-2396.

Thomas, Ciel P., "Non-Final Office Action", U.S. Appl. No. 14/704,783, dated Apr. 5, 2017, 1-16.

Unknown, , "Notice of Allowance", Korean Patent Application No. 10-2012-7027450, dated Apr. 27, 2017, 1-3.

Wong, Edna , "Final Office Action", U.S. Appl. No. 14/322,037, dated May 9, 2017, 1-18.

Wong, Edna , "Notice of Allowance", U.S. Appl. No. 14/098,000, dated May 10, 2017, 1-7.

"Notice of Allowance", Chinese Patent Application No. 201080024541.8, dated Dec. 1, 2014, 1-2.

Akhir, Sharul Kamal B. , "Malaysian Search Report", Malaysia Patent Application No. PI 2011004930, dated Feb. 26, 2015, 1.

Aslanov, N. N. , "English Language Bibliographical Information and Abstract", SU Patent No. 979325, Dec. 7, 1982, 1-3.

Bond, Jesse Q. et al., "Integrated Catalytic Conversion of gamma-Valerolactone of Liquid Alkenes for Transportation Fuels", Science, Feb. 26, 2010, vol. 327: 1110-1114.

Bozell, Joseph J. , "Connecting Biomass and Petroleum Processing with a Chemical Bridge", Science, Jul. 30, 2010, vol. 329: 522-523.

Choi, et al., "Recovery of lactic acid from sodium lactate by ion substitution using ion-exchange membrane", Separation and Purification Technology 28 (2002), Elsevier, Mar. 4, 2002, 69-79.

(56) References Cited

OTHER PUBLICATIONS

Chum, H L. et al., "Photoelectrochemistry of Levulinic Acid on Undoped Platinized n-TIO2 Powders", J. Phys. Chem, 1983, vol. 87: 3089-3093.
Conway, et al., "New Approaches to the Study of Electrochemical Decarboxylation and the Kolbe Reaction. I. The Model Reaction with Formate", Canadian Journal of Chemistry (no month, 1963), vol. 41, 1963, 21-37.
Dzik, et al., "Carboxylates as sources of carbon nucleophiles and electrophiles: comparison of decarboxylative and decarbonylative pathways", Chemical Science, 2012, vol. 3, Issue No. 9 (2012), May 3, 2012, 2671-78.
Edna, Wong , "Non-Final Office Action", U.S. Appl. No. 14/098,000, dated Oct. 13, 2016, 1-20.
Glasstone, et al., "Studies in Electrolysis Oxydation Part V11. The Electrolysis of Acetates in Non-Aqueous Solutions.", J. Chem. Soc., Jan. 1, 1936, 820-827.
Habova, et al., "Application of Electrodialysis for Lactic Acid Recovery", Czech J. Food Sci., vol. 19, No. 2 (2001), Jan. 1, 2001, 73-80.
Haufe, et al., "Bifunktionelle Verbindungen durch Kolbe-Elecktolyse", Chemie-Ing. Techn., vol. 42, No. 4, 1970, pp. 170-175, XP002751054, 1970, 1-6.
Ho, Park S. , "International Search Report", PCT US 2011/035782 (corresponding to U.S. Appl. No. 13/103,716), dated Feb. 9, 2012, 1-3.
Ho, Park S. , "Written Opinion of the International Searching Authority", PCT US 2011/035782 (corresponding to U.S. Appl. No. 13/103,716), dated Feb. 9, 2012, 1-4.
Hongyou, et al., "English Language Abstract", CN101089231A, Dec. 19, 2007, 1.
Huang, et al., "Application of electrodialysis to the production of organic acids: State-of-the-art and recent developments", Journal of Membrane Science 288 (2007), Elsevier, Nov. 25, 2006, 1-12.
Kang, Sang Yoon , "PCT International Search Report", Int. App. No. PCT/US2010/042756, dated Feb. 28, 2011, 1-3.
Kang, Sang Yoon , "PCT Written Opinion", Int. App. No. PCT/US2010/042756, dated Feb. 28, 2011, 1-4.
Keeling, Alexander W. , "Final Office Action", U.S. Appl. No. 14/206,981, dated Feb. 25, 2016, 1-20.
Keeling, Alexander W. , "Non-Final Office Action", U.S. Appl. No. 14/206,981, dated Oct. 7, 2015, 1-18.
Keeling, Alexander W. , "Non-Final Office Action", U.S. Appl. No. 13/092,685, dated May 20, 2014, 1-20.
Keeling, Alexander W. , "Notice of Allowance", U.S. Appl. No. 13/092,685, dated Feb. 19, 2015, 1-18.
Kim, Su M. , "International Search Report", PCT Application No. PCT/US2014/020786 (Corresponding to U.S. Appl. No. 14/198,026), dated Jun. 26, 2014, 1-3.
Kim, Su M. , "Written Opinion of the International Searching Authority", PCT Application No. PCT/US2014/020786 (Corresponding to U.S. Appl. No. 14/198,026.), dated Jun. 26, 2014, 1-3.
Kleidernigg, Oliver , "European Search Report", EP Patent Application No. 12739864.2, dated Nov. 18, 2015, 1-9.
Klocke, et al., "Influences on the Selectivity of the Kolbe versus the Non-Kolbe Electrolyis in the Anodic Decarboxylation of Carboxylic Acids", Electroorganic Sythesis, Nov. 2, 1992, 1-8.
Ko, et al., "Computer Translation of the Detailed Description of JP 6-271499", Japanese Patent publication 06-271499, Sep. 27, 1994, 1-8.
Kobzeva, et al., "Effect of a solvent on anode processes", Elektrokhimiya, vol. 11. No. 5, 1975, 1 page abstract.
Kokubo, Atsunori , "First Office Action", Japanese Patent Application No. 2013-550666, dated Aug. 25, 2015, 1-13.
Le, Zhikang , "Chinese Office Action", Chinese Application No. 201080024541.8, dated Jan. 21, 2014, 1-10.
Li, Maoying , "Chinese Office Action", Chinese Application No. 2011800079268, dated Sep. 12, 2014, 1-12.
Li, Maoying , "Non-Final Office Action", Chinese Patent Application No. 201180007926.8, dated Aug. 18, 2015, 1-15.
Li, Weishan , "Organic Synthesis using Kolbe reaction", Ghangzhou Chemical Industry vol. 20, No. 4, pp. 18-21, Dec. 30, 1992, 1-5.
Lu, et al., "Modeling of the mass transfer and conduction behavior in electro-electrodialysis with oil/water emulsion as the catholyte", Journal of Membrane Science 322 (2008), Elsevier, Jun. 5, 2008, 265-274.
Mendez, Zulmariam , "Final Office Action", U.S. Appl. No. 12/840,401, dated Mar. 15, 2013, 1-12.
Mendez, Zulmariam , "Final Office Action", U.S. Appl. No. 13/790,744, dated Jul. 9, 2015, 1-13.
Mendez, Zulmariam , "Final Office Action", U.S. Appl. No. 13/834,569, dated Feb. 23, 2016, 1-17.
Mendez, Zulmariam , "Final Office Action", U.S. Appl. No. 12/840,401, dated Mar. 13, 2014, 1-19.
Mendez, Zulmariam , "Final Office Action", U.S. Appl. No. 12/840,401, dated Apr. 3, 2015, 1-20.
Mendez, Zulmariam , "Final Office Action", U.S. Appl. No. 12/840,401, dated Mar. 13, 2014, 1-23.
Mendez, Zulmariam , "Non Final Office Action", U.S. Appl. No. 13/834,569, dated Jul. 15, 2015, 1-15.
Mendez, Zulmariam , "Non Final Office Action", U.S. Appl. No. 13/790,744, dated Dec. 28, 2015, 1-15.
Mendez, Zulmariam , "Non Final Office Action", U.S. Appl. No. 12/840,401, dated Jul. 30, 2013, 1-15.
Mendez, Zulmariam , "Non-Final Office Action", U.S. Appl. No. 13/790,744, dated Nov. 4, 2014, 1-11.
Mendez, Zulmariam , "Non-Final Office Action", U.S. Appl. No. 12/840,401, dated Jun. 5, 2012, 1-12.
Mendez, Zulmariam , "Non-Final Office Action", U.S. Appl. No. 12/840,401, dated Aug. 26, 2014, 1-18.
Mendez, Zulmariam , "Non-Final Office Action", U.S. Appl. No. 13/790,744, dated Mar. 20, 2014, 1-22.
Minami, et al., "Electrolysis of Fatty Acids II", Kogyo Kagaku Zasshi, vol. 53, 1950, 1 page abstract.
Moon, et al., "Competitive Anion Transport in Desalting Mixtures of Organic Acids by Batch Electrodialysis", Journal of Membrane Science 141 (1998), Elsevier, Apr. 1, 1998, 75-89.
Obermuller, , "Saponification by Sodium Ethoxide", J Chem. Soc., Abstr. 62, 1892, 1 page abstract.
Ono, et al., "Electrolysis of fatty acids I", Ind. Chem. Sect. 53, 1950, 1 page abstract.
Palaty, et al., "Continuous dialysis of carboxylic acids. Permeability of Neosepta-AMH membrane", Desalination 216 (2007), Elsevier, Oct. 1, 2007, 345-355.
Palit, Santi R. , "The Solubility of Soaps and of Some Salts in Mixtures of Solvents, One of Which Is of Glycolic Type", Utah Consortia UALC, vol. 69, Dec. 1947, 3120-29.
Pande, et al., "Studies on Kolbe's Electrosynthesis", Electrochimica Acta, Aug. 1961, vol. 4, Aug. 1961, 215-231.
Park, Sang H. , "International Search Report", PCT Application No. PCT/US2011/033636 (corresponding to U.S. Appl. No. 13/092,685), dated Feb. 8, 2012, 1-3.
Park, Sang H. , "Written Opinion of the International Searching Authority", PCT Application No. PCT/US2011/033636 (corresponding to U.S. Appl. No. 13/092,685), dated Feb. 8, 2012, 1-4.
Park, Sang Ho , "PCT International Search Report", Int. App. No. PCT/US2010/042715, dated Apr. 29, 2011, 1-3.
Park, Sang Ho , "PCT International Search Report", Int. App. No. PCT/US2010/042780, dated May 2, 2011, 1-3.
Park, Sang Ho , "PCT Written Opinion", Int. App. No. PCT/US2010/042715, dated Apr. 29, 2011, 1-4.
Park, Sang Ho , "PCT Written Opinion", Int. App. No. PCT/US2010/042780, dated May 2, 2011, 1-4.
Paul, et al., "Reactions of Sodium Metal with Aromatic Hydrocarbons", J. Am. Chem. Soc., 1956, 78 (1), Jan. 1956, 116-120.
Prado Rubio, et al., "Modeling Reverse Electro-Enhanced Dialysis for Integration with Lactic Acid Fermentation", CAPEC, Department of Chemical and Biochemical Engineering Technical University of Denmark (DTU), DK-2800 Lyngby, Denmark, 2009, Available as "A-DK-Prado Rubio-OA-1" at Docstoc.com, http://www.docstoc.com/search/modeling%20reverse%20electro~enhanced%20dialysis%20for%20integration%20with%20lactic%20acid%20fermentation?catid=0, Jan. 1, 2009, 1-2.

(56) References Cited

OTHER PUBLICATIONS

Rabjohn, et al., "Kolbe Electrosynthesis of Alkanes with Multiple Quaternary Carbon Atoms", J. Org. Chem., 1981, vol. 46, pp. 4082-4083.
Schafer, Hans-Jurgen, "Recent Contributions of Kolbe Electrolysis to Organic Synthesis", Topics in Current Chemistry, 1990, vol. 152: 91-151.
Sekine, Isao et al., "Effect of the Concentration of Acetate or Propionate on the Abnormal Phenomena in the Kolbe Reaction", Denki Kagaku, vol. 41(9), 1973, 702-707.
Shafer, Hans J., "Electrochemical Conversion of Fatty Acids", European Journal of Lipid Science and Technology, vol. 114, Issue 1, Oct. 11, 2011, 2-9.
Shin, Ju C., "International Search Report", PCT/US2014/021927 (Corresponding to U.S. Appl. No. 13/790,744), dated Jul. 10, 2014, 1-3.
Shin, Ju C., "International Search Report", PCT Application No. PCT/US2014/028842 (Corresponding to U.S. Appl. No. 13/834,569), dated Aug. 14, 2014, 1-3.
Shin, Ju C., "Written Opinion of the International Searching Authority", PCT/US2014/021927 (Corresponding to U.S. Appl. No. 13/790,744), dated Jul. 10, 2014, 1-7.
Shin, Ju C., "Written Opinion of the International Searching Authority", PCT Application No. PCT/US2014/028842 (Corresponding to U.S. Appl. No. 13/834,569), dated Aug. 14, 2014, 1-7.
Stapley, et al., "English Language Abstract", CN101336313A, Dec. 31, 2008, 1.
Thomas, Ciel P., "Non-Final Office Action", U.S. Appl. No. 14/469,878, dated Mar. 3, 2016, 1-13.
Uknown, , "Notice of Allowance", Japanese Patent Application No. 2013-550666, dated Feb. 2, 2016, 1-4.
Weiper, et al., "Mixed Kolbe Electrolysis with Sugar Carboxylic Acids", Angew. Chem. Int. Ed. Engl.;(no month, 1990) vol. 29 No. 2; pp. 195-197, 1990, 195-197.
Wong, Edna, "Final Office Action", U.S. Appl. No. 14/198,026, dated Apr. 3, 2015, 1-11.
Wong, Edna, "Final Office Action", U.S. Appl. No. 13/612,192, dated Apr. 14, 2015, 1-12.
Wong, Edna, "Final Office Action", U.S. Appl. No. 13/357,463, dated Jan. 3, 2014, 1-14.
Wong, Edna, "Final Office Action", U.S. Appl. No. 13/103,716, dated Nov. 20, 2014, 1-15.
Wong, Edna, "Final Office Action", U.S. Appl. No. 13/357,463, dated Sep. 6, 2013, 1-16.
Wong, Edna, "Final Office Action", U.S. Appl. No. 12/840,913, dated Jul. 18, 2013, 1-16.
Wong, Edna, "Final Office Action", U.S. Appl. No. 13/357,463, dated Sep. 19, 2012, 1-17.
Wong, Edna, "Final Office Action", U.S. Appl. No. 13/612,192, dated Aug. 15, 2014, 1-18.
Wong, Edna, "Final Office Action", U.S. Appl. No. 14/322,037, dated Dec. 18, 2015, 1-21.
Wong, Edna, "Final Office Action", U.S. Appl. No. 12/840,508, dated Nov. 27, 2012, 1-25.
Wong, Edna, "Final Office Action", U.S. Appl. No. 12/840,913, dated Aug. 14, 2012, 1-28.
Wong, Edna, "Final Office Action", U.S. Appl. No. 13/930,211, dated Nov. 21, 2014, 1-32.
Wong, Edna, "Non Final Office Action", U.S. Appl. No. 14/322,037, dated Mar. 29, 2016, 1-18.
Wong, Edna, "Non Final Office Action", U.S. Appl. No. 13/357,463, dated Apr. 9, 2013, 1-21.
Wong, Edna, "Non Final Office Action", U.S. Appl. No. 14/098,000, dated Dec. 29, 2015, 1-27.
Wong, Edna, "Non Final Office Action", U.S. Appl. No. 12/840,913, dated Mar. 28, 2013, 1-31.
Wong, Edna, "Non-Final Office Action", U.S. Appl. No. 12/840,913, dated Apr. 10, 2012, 1-12.
Wong, Edna, "Non-Final Office Action", U.S. Appl. No. 13/103,716, dated Jun. 24, 2014, 1-15.
Wong, Edna, "Non-Final Office Action", U.S. Appl. No. 14/322,037, dated Sep. 1, 2015, 1-18.
Wong, Edna, "Non-Final Office Action", U.S. Appl. No. 14/198,026, dated Nov. 14, 2014, 1-20.
Wong, Edna, "Non-Final Office Action", U.S. Appl. No. 13/612,192, dated Apr. 8, 2014, 1-24.
Wong, Edna, "Non-Final Office Action", U.S. Appl. No. 13/357,463, dated Jun. 4, 2012, 1-25.
Wong, Edna, "Non-Final Office Action", U.S. Appl. No. 12/840,508, dated Apr. 26, 2012, 1-32.
Wong, Edna, "Non-Final Office Action", U.S. Appl. No. 13/612,192, dated Dec. 10, 2013, 1-33.
Wong, Edna, "Non-Final Office Action", U.S. Appl. No. 13/612,192, dated Dec. 5, 2014, 1-37.
Wong, Edna, "Non-Final Office Action", U.S. Appl. No. 13/930,211, dated Jul. 23, 2014, 1-43.
Wong, Edna, "Notice of Allowance", U.S. Appl. No. 12/840,508, dated Apr. 29, 2013, 1-11.
Wong, Edna, "Notice of Allowance", U.S. Appl. No. 14/198,026, dated Aug. 4, 2015, 1-7.
Wong, Edna, "Notice of Allowance", U.S. Appl. No. 13/103,716, dated Feb. 26, 2015, 1-9.
Wong, Edna, "USPTO Office Action", U.S. Appl. No. 12/840,913, dated Nov. 16, 2011, 16 pages.
Wong, Edna, "USPTO Office Action", U.S. Appl. No. 12/840,508, dated Nov. 2, 2011, 17 pages.
Wong, Enda, "Notice of Allowance", U.S. Appl. No. 12/840,913, dated Oct. 4, 2013, 1-11.
Yi, et al., "An in situ coupling separation process of electro-electrodialysis with back-extraction", Journal of Membrane Science 255 (2005), Elsevier, Mar. 21, 2005, 57-65.
Eberson, L, "Studies on the Kolbe Electrolytic Synthesis", Acta. Chem. Scand., vol. 17, No. 7, 1963. pp. 2004-2018, XP002751055, 1963, 1-15.
Keeling, Alexander W., "Notice of Allowance", U.S. Appl. No. 14/206,981, dated Jul. 14, 2016, 1-10.
Mendez, Zulmariam, "Final Office Action", U.S. Appl. No. 13/790,744, dated Aug. 9, 2016, 1-18.
Mendez, Zulmariam, "Non Final Office Action", U.S. Appl. No. 13/834,569, dated Jul. 22, 2016, 1-15.
Mendez, Zulmariam, "Non-Final Office Action", U.S. Appl. No. 13/790,744, dated Mar. 7, 2017, 1-22.
Ritter, Thomas, "European Search Report", European Patent Application No. 118149293, dated Sep. 12, 2016, 1-11.
Ritter, Thomas, "European Search Report", European Patent Application No. 147608897, dated Sep. 12, 2016, 1-11.
Ritter, Thomas, "European Search Report", European Patent Application No. 147627293, dated Sep. 12, 2016, 1-11.
Ritter, Thomas, "European Search Report", European Patent Application No. 147608889, dated Sep. 12, 2016, 1-7.
Sharkey, et al., "2,7-Dimethyl-2,7-Dinitrooctane", Organic Syntheses., vol. 41, Jan. 1, 1961 (Jan. 1, 1961), p. 24, Jan. 1, 1961, 1-5.
Thomas, Ciel P., "Final Office Action", U.S. Appl. No. 14/469,878, dated Nov. 3, 2016, 1-7.
Thomas, Ciel P., "Notice of Allowance", U.S. Appl. No. 14/469,878, dated Feb. 15, 2017, 1-20.
Unknown, , "English Transation of Non Final Office Action", Korean Patent Application No. 10-2012-7027450, dated Oct. 27, 2016, 1-5.
Unknown, , "Non-Final Office Action", Korean Patent Application No. 10-2012-7027450, dated Oct. 27, 2016, 1-3.
Unknown, , "Notice of Allowance", Chinese Patent Application No. 201180007926.8, dated May 24, 2016, 1-4.
Wong, Edna, "Final Office Action", U.S. Appl. No. 14/098,000, dated Feb. 28, 2017, 1-19.
Wong, Edna, "Final Office Action", U.S. Appl. No. 14/322,037, dated Jul. 25, 2016, 1-21.
Wong, Edna, "Final Office Action", U.S. Appl. No. 14/098,000, dated Jun. 6, 2016, 1-34.
Wong, Edna, "Non-Final Office Action", U.S. Appl. No. 14/322,037, dated Nov. 23, 2016, 1-10.
Wong, Edna, "Non-Final Office Action", U.S. Appl. No. 14/098,000, dated Oct. 13, 2016, 1-18.

(56) References Cited

OTHER PUBLICATIONS

Zhuo, et al., "Degradation of Perfuluorinated Compounds on a Boron-Doped Diamond Electrode", Electrochimica Acta, Elsevier Science Publishers, Barking, GB, vol. 77, Apr. 14, 2012 (Apr. 14, 2012), pp. 17-22, Apr. 14, 2012, 17-22.
Eberson, L., Studies on the Kolbe Electrolytic Synthesis, Acta Chemica Scandinavica 17 (1963) No. 5 1196-1202.
Extended European Search Report in EP 11772799.0 dated Aug. 25, 2016 (5 pages).
Extended European Search Report in EP14760889.7 dated Sep. 20, 2016 (11 pages).
International Search Report and Written Opinion in PCT/US2014/021927 dated Jul. 10, 2014 (10 pages).
Sharkey et al., 2,7-Dimethyl-2,7-Dinitrooctane, Organic Syntheses, Coll. vol. 5, p. 445 (1973); vol. 41, p. 24 (1961) (5 pages).

\* cited by examiner

CUSTOM IONIC LIQUID ELECTROLYTES FOR ELECTROLYTIC DECARBOXYLATION

RELATED APPLICATIONS

This patent application is a divisional of, and claims priority to, U.S. patent application Ser. No. 14/206,981 (the "'981 application"), filed on Mar. 12, 2014 and titled "Custom Ionic Liquid Electrolytes for Electrolytic Decarboxylation," now U.S. Pat. No. 9,493,882, which claims the benefit of U.S. Provisional Patent Application No. 61/778,037, file Mar. 12, 2013. The '981 application is also a continuation-in-part of U.S. application Ser. No. 12/840,401, filed Jul. 21, 2010, now abandoned, Ser. No. 12/840,913, filed Jul. 21, 2010, now U.S. Pat. No. 8,647,492, Ser. No. 12/840,508, filed Jul. 21, 2010, now U.S. Pat. No. 8,506,789, Ser. No. 13/092,685, filed Apr. 22, 2011, now U.S. Pat. No. 9,051,656. These provisional and non-provisional patent applications are expressly incorporated herein by reference.

GOVERNMENT RIGHTS

At least part of the technology disclosed in this patent application may have been funded by the United States Government under Award No. 2012-10008-20263 from the United States Department of Agriculture, National Institute of Food and Agriculture. The United States Government may have certain rights in the invention.

BACKGROUND

1. Field of the Invention

The present invention describes a method of electrochemical synthesis of organic compounds using an electrochemical decarboxylation process (EDP), and more specifically such processes using custom electrolytes and ionic liquids. The EDP can be used to converts alkali salts of a variety of carboxylic acids to different hydrocarbon products. Carboxylic acids ($RCO_2H$) make up a board class of organic compounds, where R can be an alkyl group, cycloalkyl group, an alkyenyl, and alkynyl group and an aryl group. The R group can also contain a hydrocarbon that may possess a heteroatom such as O, S, N, etc. The electrochemical decarboxylation disclosed in this patent removes $CO_2$ from the carboxylic acid and creates a high energy radical or carbocation which can form carbon-carbon or carbon hydrogen bonds with other species present in solution. This process can be used to synthesize a variety of different types of organic compounds such as saturated hydrocarbons, diols, esters, olefins, aryl-alkyl compounds, etc. The electrochemical decarboxylation process is advantageous to other methods conventionally used to synthesize these compounds because it can be performed at moderate conditions and does not require the use of catalyst.

2. Description of the Related Art

Conventionally, electrochemical decarboxylation reactions are performed in polar organic solvents. Due to the versatility of the process there is not a single polar organic solvent that meets all the requirements needed for a universal electrolyte that can be applied to the decarboxylation of the vast amounts of carboxylic acids available. Other limitations of using common polar organic electrolytes are the limited carboxylic acid solubility and the electrolyte can be electrochemically oxidized during the decarboxylation process. The lack of a universal electrolyte limits the carboxylic acids that can be processed with the electrochemical decarboxylation process, and also limits the commercial application of such a process as the current efficiency and product selectivity is low because of the high number of side products that form from the oxidation of the solvent. Also, the use of polar organic solvents counter balances the environmental benefits afforded by the use of carboxylic acid precursors and the electrochemical decarboxylation process.

It would be advantageous to find an electrolyte system that has a high conductivity, is electrochemically stable, and can be modified for specific reactions to provide high solubility of the carboxylic acid precursors, low solubility of the hydrocarbon products, and minimizes the side reactions involving the electrolyte. It is one aim of the disclosed invention to prepare custom ionic liquids for use as electrolytes in the electrochemical decarboxylation, being designed for the specific decarboxylation process of interest. Iionic liquids are defined as liquids composed of ions that are fluid around or below 100° C., and exhibit low vapor pressure and can be reused with the appropriate design considerations. Ionic liquids are considered to be "designer" solvent systems, because the properties of the ionic liquids can be modified by changing the cation and anion of the liquid, and/or by modifying the structure of the cation and anion. Such an electrolyte system will improve the applicability and efficiency of the electrochemical decarboxylation process, distinguishing it as an alternative preparation method that is more economically and environmentally sustainable than the convention synthesis routes.

SUMMARY OF THE INVENTION

In one aspect, an electrolytic cell is disclosed. The cell includes an anode, a cathode, and a composition having compounds of formulas $R^1COOM$ and $R^2COOM$ in an ionic liquid; wherein each of $R^1$ and $R^2$ is independently selected from unsubstituted and substituted alkyl, unsubstituted and substituted cycloalkyl, unsubstituted and substituted heterocyclyl, substituted and unsubstituted alkenyl, substituted and unsubstituted alkynyl, substituted and unsubstituted aryl, and substituted and unsubstituted heteroaryl; and each M is independently an alkali metal.

In another aspect, a method of making a compound of formula $R^1$-$R^2$, includes providing compounds of formulas $R^1COOM$ and $R^2COOM$ in an ionic liquid; applying an electric current to the ionic liquid; wherein each of $R^1$ and $R^2$ is independently selected from unsubstituted and substituted alkyl, unsubstituted and substituted cycloalkyl, unsubstituted and substituted heterocyclyl, substituted and unsubstituted alkenyl, substituted and unsubstituted alkynyl, substituted and unsubstituted aryl, and substituted and unsubstituted heteroaryl; and each M is independently an alkali metal.

In some embodiments, substitutions on substituted alkyl, cycloalkyl, heterocyclyl, alkenyl, alkynyl, aryl, and heteroaryl are selected from halogen, unsubstituted $C_{1-8}$ alkyl, —CN, —$NO_2$, =O, —C(O)$R^A$, —$CO_2R^A$, —C(O)$NR^AR^B$, —$OR^A$, —OC(O)$R^A$, —OC(O)$NR^AR^B$, —$NR^C(O)R^A$, —$NR^C(O)NR^AR^B$, —$NR^AR^B$, —$NR^CCO_2R^A$, —$NR^CS(O)_2R^A$, —$SR^A$, —S(O)$R^A$, —$S(O)_2R^A$, —$S(O)_2NR^AR^B$; wherein each of $R^A$, $R^B$, and $R^C$, when present, is independently selected from the group consisting of: —H, unsubstituted $C_{1-8}$ alkyl, unsubstituted $C_{2-8}$ alkenyl, or unsubstituted $C_{2-8}$ alkynyl.

In some embodiments, the substitutions on substituted alkyl, cycloalkyl, heterocyclyl, alkenyl, alkynyl, aryl, and heteroaryl are located geminal to the group —COOM.

In some embodiments, the ionic liquid has the formula [(R')(R")(R''')(R'''')X]; wherein X is selected from substituted or unsubstituted pyridinium, substituted or unsubstituted pyridazinium, substituted or unsubstituted pyrimidinium, substituted or unsubstituted pyrazinium, substituted or unsubstituted pyrrolidiniutn, substituted or unsubstituted imidazolium, substituted or unsubstituted pyrazolium, substituted or unsubstituted thiazolium, substituted or unsubstituted oxazolium, substituted or unsubstituted triazolium, phosphonium, and ammonium; and wherein each of R', R", R''', and R'''' is independently selected from fluoro, phosphinates, alkylphosphinates, alkylthiophosphinates, sulfates, sulphonates, amides, tosylates, alum mates, borates, arenates, cuprates, nitrates, carboxylates, hydrogen, unsubstituted and substituted alkyl, unsubstituted and substituted cycloalkyl, unsubstituted and substituted heterocyclyl, substituted and unsubstituted alkenyl, substituted and unsubstituted alkynyl, substituted and unsubstituted aryl, and substituted and unsubstituted heteroaryl, provided that when X is ammonium or phosphonium, then each of R', R", R''', and R'''' may also independently be hydrogen.

The electrolytic cell or method wherein substitutions on substituted alkyl, cycloalkyl, heterocyclyl, alkenyl, alkynyl, aryl, and heteroaryl are selected from halogen, unsubstituted $C_{1-8}$ alkyl, —CN, —NO$_2$, =O, —C(O)R$^A$, —CO$_2$R$^A$, —C(O)NR$^A$R$^B$, —OR$^A$, —OC(O)R$^A$, —OC(O)NR$^A$R$^B$, —NR$^C$C(O)R$^A$, —NR$^C$C(O)NR$^A$R$^B$, —NR$^A$R$^B$, —NR$^C$CO$_2$R$^A$, —NR$^C$S(O)$_2$R$^A$, —SR$^A$, —S(O)R$^A$, —S(O)$_2$R$^A$, —S(O)$_2$NR$^A$R$^B$; wherein each of R$^A$, R$^B$, and R$^C$, when present, is independently selected from the group consisting of: H, unsubstituted $C_{1-8}$ alkyl, unsubstituted $C_{2-8}$ alkenyl, or unsubstituted $C_{2-8}$ alkynyl.

In some embodiments, each of R', R", R''', and R'''' is the same. In some embodiments, at least one of R', R", R''', and R'''' is different from the others.

In some embodiments, the method also includes contacting a compound of formula R$^1$COOH with an alkaline hydroxide of formula MOH to provide a compound of formula R$^1$COOM. In some embodiments, the method also includes contacting a compound of formula R$^2$COOH with an alkaline hydroxide of formula MOH to provide a compound of formula R$^2$COOM.

In some embodiments, the method also includes heating the ionic liquid. In some embodiments, the method also includes providing the ionic liquid in an electrolytic cell.

In some embodiments, the electrolytic cell includes an anode and a cathode in separate compartments, and the ionic liquid is in the compartment with the anode, some embodiments, the compartments are separated by an alkaline-ion permeable membrane.

In some embodiments, each M is sodium. In some embodiments, R$^1$ and R$^2$ are the same. In some embodiments, R$^1$ and R$^2$ are different.

In some embodiments, the method also includes contacting the ionic liquid with an organic solvent. In some embodiments, the method also includes mixing the ionic liquid with an organic solvent.

In some embodiments, the method includes contacting the ionic liquid with a supporting electrolyte. In some embodiments, the method includes mixing the ionic liquid with a supporting electrolyte. In some embodiments, the supporting electrolyte is selected from alkali metal hydroxide, alkali metal salts, tetrafluoroborate, tetramethylammonium hexafluorophosphate, tetrabutylammonium tetrafluoroborate, tetramethylammonium perchlorate, and tetraethylammonium perchlorate.

DETAILED DESCRIPTION

Figure 1:
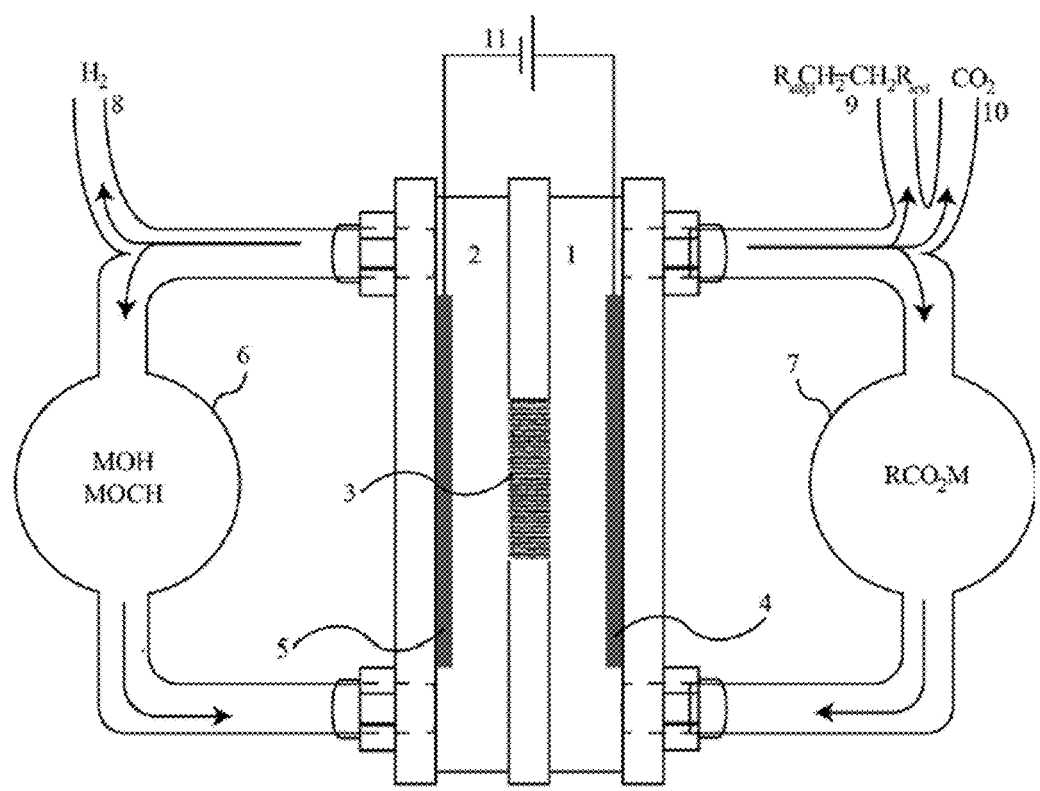
FIG. 1 shows a schematic drawing of an electrochemical cell that may be used to decarboxylate the alkali metal salts of the carboxylic acids using a custom IL electrolyte.

In one aspect, an electrolytic cell is disclosed. The cell includes an anode, a cathode, and a composition having compounds of formulas R$^1$COOM and R$^2$COOM in an ionic liquid. In another aspect, a method of making a compound of formula R$^1$-R$^2$, includes providing compounds of formulas R$^1$COOM and R$^2$COOM in an ionic liquid and applying an electric current to the ionic liquid. As a result, the compounds of formulas R$^1$COOM and R$^2$COOM are both decarboxylated and result in a compound of formula R$^1$-R$^2$.

Each of R$^1$ and R$^2$ is independently selected from unsubstituted and substituted alkyl, unsubstituted and substituted cycloalkyl, unsubstituted and substituted heterocyclyl, substituted and unsubstituted alkenyl, substituted and unsubstituted alkynyl, substituted and unsubstituted aryl, and substituted and unsubstituted heteroaryl, and each M is independently an alkali metal. As a result, a great variety of products can be obtained from practicing the disclosed method.

Substitutions on substituted alkyl, cycloalkyl, heterocyclyl, alkenyl, alkynyl, aryl, and heteroaryl include: halogen, unsubstituted $C_{1-8}$ alkyl, —CN, —NO$_2$, =O, —C(O)R$^A$, —CO$_2$R$^A$, —C(O)NR$^A$R$^B$, —OR$^A$, —OC(O)R$^A$, —OC(O)NR$^A$R$^B$, —NR$^C$C(O)R$^A$, —NR$^C$C(O)NR$^A$R$^B$, —NR$^A$R$^B$, —NR$^C$CO$_2$R$^A$, —NR$^C$S(O)$_2$R$^A$, —SR$^A$, —S(O)R$^A$, —S(O)$_2$R$^A$, —S(O)$_2$NR$^A$R$^B$; wherein each of R$^A$, R$^B$, and R$^C$, when present, is independently selected from the group consisting of: —H, unsubstituted C alkyl, unsubstituted $C_{2-8}$ alkenyl, or unsubstituted $C_{2-8}$ alkynyl.

In some embodiments, the substitutions on substituted aikyl, cycloalkyl, heterocyclyl, alkenyl, alkynyl, aryl, and heteroaryl are located geminal to the group —COOM.

Novel electrolyte systems designed for the electrochemical decarboxylation process are provided which comprise of at least one ionic liquid (IL) electrolyte. The cation and anion of the IL electrolyte are chosen such that the carboxylic acid being decarboxylated has a high solubility and the product of the decarboxylation is easily separated from the IL electrolyte. The IL electrolyte is also tuned for high electrochemical stability in the required potential range, and low chemical reactivity to species generated by the decarboxylation process. Some non-limiting examples of the cations that can be used to design the IL electrolyte disclosed in this patent are pyridinium, imidazolium, phosphonium, and ammonium, and common choices for the anion may be selected from the groups of halides, sulfates, nitrates, and carboxylates. The ability to combine different cations and anions and to modify the substituents on the cations and anions provides an electrolyte system that can be specifically designed for a particular combination of carboxylic acid and decarboxylation product.

The electrochemical decarboxylation is a well-known technique used to generate radicals for synthetic applications and is characterized as either Kolbe electrolysis or non-Kolbe electrolysis. The term Kolbe electrolysis is used to define the decarboxylation of carboxylic acids leading to radicals that then combined forming either homocoupling or heterocoupling products, and can also add to double bonds. A generic example of decarboxylation leading to homocoupling is shown below.

$$2RCO_2H \rightarrow R\text{-}R + 2CO_2 + 2e^- + 2H^+$$

The term, non-Kolbe electrolysis is used to define the decarboxylation of carboxylic acids that lead to the formation of carbocations from a two electron oxidation. The carbon cation can then participate in a number of electrophilic reactions such as heck-type reactions, substitution and addition reactions, and heteroatom bond formation. A generic example of decarboxylation leading to an electrophilic substitution reaction is shown below.

$$RCO_2H + Ar\text{-}H \rightarrow R\text{-}Ar + CO_2 + 2e^- + 2H^+$$

In one embodiment, the decarboxylation is performed on alkyl salts of carboxylic acids. The saponification of carboxylic acid follows from the generally accepted procedure of reacting the carboxylic acid with an alkali metal base (MOH) at an elevated temperature. Some non-limiting examples of alkali metal bases are lithium hydroxide, sodium hydroxide, potassium hydroxide. A genetic neutralization reaction is written below.

$$RCO_2H + MOH \rightarrow RCO_2M + H_2O$$

The decarboxylation of the alkyl salts follow the same general reaction schemes as was shown for the carboxylic acids. In one embodiment, the decarboxylation of the sodium salts is performed using a two compartment electrochemical cell, afforded via a NaSelect® membrane.

Carboxylic acids are becoming a popular substrate to perform the synthesis of industrially important compounds as they are economically and environmentally friendly. One application that they are being investigated for, is as alternatives to organohalides in the Heck reaction for the formation of carbon-carbon double bonds. Replacing the organohalide with a carboxylic acid is more environmentally friendly, because $CO_2$ and $H_2$ are the only by-products formed instead of the halide by-products produced conventionally. They are also being investigated as substrates for cross-coupling reactions where the carboxylic acid can act as either the nucleophilic or electrophilic coupling partner. This is advantageous as there are a large number of carboxylic acids available commercially, which are more economical than the conventionally used organohalides and/or organometallic reagents.

While the systems describe above benefit from the availability and low cost of carboxylic acids, they still require catalyst and high temperatures to promote the transformations. The electrolysis method disclosed in the present patent does not require the use of catalyst and can be perform at moderate temperatures and reaction conditions. And while the Kolbe electrolysis is well known, the method would be improved by the use of a designable electrolyte system that increases the solubility of the carboxylic acid, provides high conductivity and stability, and facilitates in product isolation.

Some terms and their definitions that will be used throughout the description follows. "Ionic liquid," is defined as organic salts that melts below 100° C. "Hydrocarbon," is defined as a compound consisting of carbon and hydrogen and can refer to saturated or unsaturated compounds. "Carboxylic acid," is a compound with the general formula $RCO_2H$, where the "R" can represent a variety of groups, for example saturated or unsaturated hydrocarbon chains. "Decarboxylation," herein refers to the process of removing $CO_2$ from a compound, specifically from a carboxylic acid or carboxylate anion. "Substituent" and "functional group" as used interchangeably and herein refer to an atom or group of atoms that has substituted a hydrogen atom on a carbon chain of a hydrocarbon. "Alkyoxy", herein refers to a straight-chain or branched alkyl group bound via oxygen atom.

In some embodiments, the ionic liquid has the formula [(R')(R'')(R''')(R'''')X]; wherein X is selected from substituted or unsubstituted pyridinium, substituted or unsubstituted pyridazinium, substituted or unsubstituted pyrimidinium, substituted or unsubstituted pyrazinium, substituted or unsubstituted pyrrolidinium, substituted or unsubstituted imidazolium, substituted or unsubstituted pyrazolium, substituted or unsubstituted thiazolium, substituted or unsubstituted oxazolium, substituted or unsubstituted triazolium, phosphonium, and ammonium; and wherein each of R', R'', R''', and R'''' is independently selected from fluoro, phosphinates, alkylphosphinates, alkylthiophosphinates, sulfates, sulphonates, amides, tosylates, aluminates, borates, arenates, cuprates, nitrates, carboxylates, hydrogen, unsubstituted and substituted alkyl, unsubstituted and substituted cycloalkyl, unsubstituted and substituted heterocyclyl, substituted and unsubstituted alkenyl, substituted and unsubstituted alkynyl, substituted and unsubstituted aryl, and substituted and unsubstituted heteroaryl, provided that when X is ammonium or phosphonium, then each of R', R'', R''', and R'''' may also independently be hydrogen.

Substitutions on substituted alkyl, cycloalkyl, heterocyclyl, alkenyl, alkynyl, aryl, and heteroaryl are selected from halogen, unsubstituted $C_{1-8}$ alkyl, $-CN$, $-NO_2$, $=O$, $-C(O)R^A$, $-CO_2R^A$, $-C(O)NR^AR^B$, $-OR^A$, $-OC(O)R^A$, $-OC(O)NR^AR^B$, $-NR^CC(O)R^A$, $-NR^CC(O)NR^AR^B$, $-NR^AR^B$, $-NR^CCO_2R^A$, $-NR^CS(O)_2R^A$, $-SR^A$, $-S(O)R^A$, $-S(O)_2R^A$, $-S(O)_2NR^AR^B$; wherein each of $R^A$, $R^B$, and $R^C$, when present, is independently selected from the group consisting of: $-H$, unsubstituted $C_{1-8}$ alkyl, unsubstituted $C_{2-8}$ alkenyl, or unsubstituted $C_{2-8}$ alkynyl.

In some embodiments, each of R', R'', R''', and R'''' is the same. In some embodiments, at least one of R', R'', R''', and R'''' is different from the others. In some embodiments, at least two of R', R'', R''', and R'''' are different from the others. In some embodiments, at least three of R', R'', R''', and R'''' are different from the others.

In one aspect, a method using custom ionic liquid electrolytes in electrochemical decarboxylation processes (EDP) is disclosed. The cation and anion of the ionic liquid electrolyte will be chosen based on the specific type of carboxylic acid precursor being decarboxylated in the electrolytic cell, and the hydrocarbon product that is produced.

The choice of cation affects the electrochemical and thermal stability of the IL electrolyte as well as the melting point, hydrophilicity/lipophilicity, and miscibility. An example of changing the ionic liquid cation for different synthesis requirements is the need to use a phosphonium cation based ionic liquids in systems where there are active metals or strong bases present, instead of ionic liquids based on the imidazolium cation which have been applied to alkene oligomerization, alkylation, and acylations reactions. The number, type and size of the substituents connected to the cation are known to affect the melting point and miscibility of the IL electrolyte, while the choice of anion is known to affect the solubility, miscibility and oxidative stability of the IL electrolyte.

In one embodiment, the cation of the IL electrolyte is based on one of following classes listed as non-liming examples, the pyridinium, pyridazinium, pyrimidinium, pyrazinium, pyrrolidinium, imidazolium, pyrazolium, thiazolium, oxazolium, triazoliutn, phosphonium, and ammonium. Each of the aforementioned cations can be optionally substituted or unsubstituted. Each of these cations classes have up to four sites that different substituents ($R_x$) can be located, which provide further means of designing the cation for the specific electrolysis. The substituents can be independently selected from hydrogen, halogens, $C_1$-$C_{25}$ saturated and non-saturated alkane or alkene groups with or without hetero atoms of oxygen, nitrogen, sulfur, or an aryl group or a substituted aryl group. The substituents on a cation can all be of the same type of group, or the cation can have substituents from a variety of different types of groups. The cation of the IL electrolyte should be chosen so it is either inactive in the electrochemical window that the cell is operated in, or it should be chosen to have a low reduction potential. The later choice would be in cases where the electrolysis of interest occurs at the anode and the low reduction potential of the IL electrolyte helps reduce the operating potential of the cell.

In one example of utility a phosphonium based cation is used, in which there can be four substituents which are conventionally hydrocarbon groups, and upon changing the size or type of the group the physical properties of the IL electrolyte are modified. In one case the four substituents are made up of three hexyl groups and one tetradecyl group, in another case the substituents are three butyl groups and one methyl group, or three butyl groups and a tetradecyl group, or three butyl groups and an ethyl group, or three butyl groups and an octyl group. In another example of utility imidazolium cations are used with different substituents present. In one case the three substituents are two methyl groups and one ethyl group, in another case the substituents are two methyl groups and one butyl group, or hydrogen, one methyl and one ethyl group. In another example of utility a pyrrolidinium based cation is used with different substituents present. In one case the three substituents are one hydrogen, one methyl and one butyl group, or in another case there are two hydrogens and one butyl group.

The anion of the IL electrolyte may be selected from the groups of halides, phosphinates, alkylphosphinates, alkylthiophosphinate, sulphonate, amides, tosylates, aluminates, borates, arenates, cuprates, sulfates, nitrates, and carboxylates. In one embodiment, the anion of the IL electrolyte is chosen such that it is stable in the electrochemical window that the cell is operated at, thus it does not partake in any reactions at the anode. In another embodiment, the anion of the IL electrolyte will be chosen so that it is similar to the carboxylate being processed in the cell. The similarity of the anion of the IL electrolyte and the carboxylate being decarboxylated increases the solubility of the later. One of the differences between the carboxylate used in the IL electrolyte and the carboxylate being process can be that the oxidation potential of the former is larger, thus promoting the formation of the desired hydrocarbon. In another embodiment, the anion of the ionic liquid will be the same as the carboxylate that is being processed in the cell. In this embodiment, any oxidation of the IL electrolyte will form the same product as the oxidation of the carboxylate being process in the cell. It should be clear to one experience in the field that the anion of the IL electrolyte should be chosen to primary reduce the side reactions at the anode, before considering the other properties that the anion affects.

In some embodiments, the method includes contacting a compound of formula $R^1COOH$ with an alkaline hydroxide of formula MOH to provide a compound of formula $R^1COOM$. In some embodiments, the method also includes contacting a compound of formula $R^2COOH$ with an alkaline hydroxide of formula MOH to provide a compound of formula $R^2COOM$.

In some embodiments, the method also includes heating the ionic liquid. In some embodiments, the method also includes providing the ionic liquid in an electrolytic cell.

In some embodiments, the method also includes contacting the ionic liquid with an organic solvent. In some embodiments, the method also includes mixing the ionic liquid with an organic solvent.

In some embodiments, the method includes contacting the ionic liquid with a supporting electrolyte. In some embodiments, the method includes mixing the ionic liquid with a supporting electrolyte. In some embodiments, the supporting electrolyte is selected from alkali metal hydroxide, alkali metal salts, tetrafluoroborate, tetramethylammonium hexafluorophosphate, tetrabutylammonium tetrafluoroborate, tetramethylammonium perchlorate, and tetraethylammonium perchlorate.

In one embodiment, the IL electrolyte is prepared following standard procedures found in the literature, of which there are many routes that can be used to prepare pure ionic liquids with different cations and anions. In another embodiment, the IL electrolyte is prepared by performing an ion exchange with an ionic liquid that already has the cation of interest. For a non-limiting example, a phosphonium carboxylate IL electrolyte can be prepared by mixing a phosphonium halide ionic liquid with aqueous alkali carboxylate salt solution. The halide and the carboxylate exchange cations, allowing the sodium halide aqueous phase to then be separated from the phosphonium carboxylate ionic liquid. Some non-limiting examples of carboxylate anions are acetate, propionate, lactate, butanate, pentoate, hexanoate, heptanoate, octanoate, laurate, oleate, stearate, linoleate, palmitate, myristrate, levulinate, valerate, benzoate, naphthenate and naphthoate.

In some embodiments, the electrolytic cell includes an anode and a cathode in separate compartments, and the ionic liquid is in the compartment with the anode. In some embodiments, the compartments are separated by an alkaline-ion permeable membrane.

In one embodiment, the IL electrolyte is used in a one compartment cell and the carboxylic acid or a salt of the carboxylic acid is dissolved into the IL electrolyte. In this embodiment, the IL electrolyte needs to be designed to limit the number of side reactions at the anode, provide a low potential reduction reaction at the cathode and have a high conductivity. The first requirement is to increase the current efficiency and product selectivity, while the second two requirements are in order to minimize the operating potential of the cell.

In another embodiment, a two compartment electrolytic cell schematically represented in FIG. 1 is used, which has two compartments separated by a (3) membrane, for example a NaSelect® membrane. In such an embodiment, the anolyte and the catholyte can be comprised of an IL electrolyte, each designed specifically for the reactions that occur in the two separate compartments, or each being the same electrolyte with different and/or the same species dissolved in them. In another embodiment, the anolyte can be comprised of an ionic liquid electrolyte, and the catholyte can be comprised of a polar solvent electrolyte such as an aqueous based electrolyte.

The anolyte is fed into the (1) anode compartment and during electrolysis is oxidized at the (4) anode's surface causing the decarboxylation of the carboxyl functional group forming a radical and $CO_2$. On the other side of the cell the reduction of the catholyte is occurring and to maintain charge balance a positive ion must transfer from the anode to the cathode, and in the case when the anolyte and catholyte are separated there needs to be a path for the positive ions to transfer between compartments. In one embodiment, an (3) ion conducting membrane selectively transfers alkali ions ($M^+$), including but not limited to the ions of sodium, lithium, and potassium, from the anolyte to the catholyte under the influence of an applied electrical field. In one embodiment, a NaSelect® membrane selectively transfers sodium ions between the anolyte and catholyte.

In one embodiment, the (3) ion conductive membrane is between 10 and 5000 microns thick, or more preferable the membrane is between 100 and 1000 microns thick, or even more preferable the membrane is between 200 and 700 microns thick. In one embodiment, the membrane is in the form of disk with diameters between 0.25-25 cm, even more preferably the diameter is between 1.27 and 12.7 cm, or most preferably between 2.54 and 7.62 cm and are assembled in a scaffold. In another embodiment, the membrane is in the form of a cylinder with a diameter between 0.25-2.5 cm, even more preferably between 1.27 and 12.7 cm, or most preferably between 2.54 and 7.62 cm.

Thus, in one embodiment, the electrochemical cell can be in a parallel plate configuration which uses flat membranes, for example as shown in FIG. 1. In another embodiment, the electrochemical cell is in a tubular configuration which uses tubular electrodes and membranes. It should be clear to one skilled in the art that the cell configurations listed above both have advantages and disadvantages which would lead to one being chosen over the other depending on the requirements of the specific carboxylic salt being decarboxylated. It should also be clear to one skilled in the art; the processes described can be applied in a variety of cell designs.

The (4) anode can comprise any suitable material that allows oxidation reactions to occur in the (1) anolyte compartment when an (11) electrical field is applied between the anode and cathode. Some non-limiting examples of anode materials include, but are not limited to, platinum, titanium, nickel, cobalt, iron, stainless steel, lead dioxide, metal alloys, combination thereof, and other known or novel anode materials. In one embodiment, the anode may comprise of iron-nickel alloys such as KOVAR® or INVAR®. In other embodiments, the anode may comprise carbon based electrodes such as boron doped diamond, glassy carbon, and synthetic carbon. Additionally, in some embodiments the anode comprises a dimensionally stable anode (DSA), which may include, but is not limited to, rhenium dioxide and tantalum pentoxide on a titanium substrate.

The (5) cathode may also be fabricated of any suitable cathode material that allows the reduction of water or methanol producing hydroxide or methoxide ions and hydrogen gas. The cathode may comprise of the materials used for the (4) anode or the (5) cathode may comprise of materials different from that used as the anode. Some non-examples of suitable cathode materials include without limitation, nickel, stainless steel, graphite, and any other suitable cathode material that is known or novel.

In one embodiment, the electrodes have a smooth morphology such as a foil or thin film. In another embodiment, the (4) anode and (5) cathode have a high surface area morphology, for example but not limited to, a foam, grit, or other porous structure. In one embodiment, the (4) anode and (5) cathode have the same morphology, while in another embodiment, electrodes have a different morphology.

In one embodiment, the electrolyte is feed into the cell without an ion conductive membrane. The electrolyte comprises of an IL electrolyte and a carboxylic acid or an alkyl salt of a carboxylic acid. In another embodiment, the (7) anolyte is feed into the (2) anolyte compartment and the (6) catholyte is feed into the (2) catholyte compartment which are separated by an (3) ion conductive membrane. The (7) anolyte consist of an IL electrolyte and an alkali metal salt of a carboxylic acid. The carboxylate that is dissolved into the IL electrolyte is chosen based on the desired products of the decarboxylation reaction, and can be aliphatic or aromatic in nature. The carboxylate ion can contain various functional groups, and or heteroatoms. In one embodiment, multiple carboxylates are dissolved in the IL electrolyte and decarboxylated in the electrolysis cell simultaneously, this leads to homo and hetero coupling.

The (7) anolyte solution may comprise of a mixture of the IL electrolyte and a polar solvent. For some non-limiting examples of suitable polar solvents include with-out limitation, water, methanol, ethanol, isopropanol, n-propanol, acetone, acetonitrile, dioxane, butanol, DMSO, $CS_2$, diethyl carbonate, ethylene carbonate, and glycerol. In other embodiment, the anolyte solution may comprise of mixture of an IL electrolyte and an aromatic solvent. Some non-limiting examples of aromatic solvents are benzene, xylene, nitro benzene, and toluene. In some embodiments, the anolyte solution may comprise of a mixture of an IL electrolyte and a non-polar organic solvent. Some examples of non-polar organic solvents are hexane, cyclohexane, pentadecane, petroleum ethers, and dodecane. In such embodiments the carboxylate salts are soluble in the IL electrolyte and the products of the decarboxylation are soluble in the non-polar solvent and thus are easily separated from the reactants.

Certain alkali ion conductive membranes, for example NaSICON and LiSICON-type membranes, have a high temperature tolerance and thus the anolyte solution may be heated to a higher temperature without substantially affecting the temperature of the catholyte solution or the functionality of the membrane. This means the IL electrolyte can be used at high temperatures and/or mixed with molten salts or acids which help dissolve the carboxylate salts in the anolyte. Thus, in one embodiment, the anolyte is a mixture of an IL electrolyte and a molten salt of the carboxylate anion that is being oxidized.

The anolyte solution may optionally contain a supporting electrolyte which is soluble in the IL electrolyte and provides high electrolyte conductivity in the anolyte solution. Non-limiting examples of supporting electrolytes include alkali metal hydroxide, alkali metal salts, tetrafluoroborate, tetramethylammonium hexafluorophosphate, tetrabutylammonium tetrafluoroborate, tetramethylammonium perchlorate, and tetraethylammonium perchlorate. It should be appreciable to those skilled in the art that other soluble ionic compounds may be used.

The (6) catholyte may comprise of a solvent that is the same or different than the (7) anolyte solvent. This is afforded because the (3) ion conductive membrane isolates the compartments from each other. Thus, the (7) anolyte and (6) catholyte solvents may be separately selected specifically for the reactions that occur in each compartment and/or the solubility of the chemicals required for the specific reactions. This permits one to design an inexpensive (6) catholyte which may have different properties than the (7) anolyte, for example to have high ionic conductivity.

In one embodiment, the (6) catholyte is comprised of water and an unsaturated alkali hydroxide. The hydroxide concentration is between 0.1-50% by weight, or more preferably between 5-25% by weight, or most preferably between 7-15% by weight. Another embodiment, the (6) catholyte consists of alkali methylate. The temperature of the (6) catholyte may or may not be the same temperature of the (7) anolyte.

When a potential is applied to the (5) cathode a reduction reaction occurs. When the catholyte solution is an aqueous based solution, water is reduced to (8) hydrogen gas and hydroxide ions. The hydroxide formed can then combine with the alkali ion that is transported through the (3) ion conducting membrane causing the alkali hydroxide concentration of the catholyte to increase as the electrolysis is performed.

It will be appreciated that the catholyte product stream comprises of a base which may be used to neutralize the carboxylic acid to produce the alkali metal salt of the carboxylic acid. Thus, the base consumed by the acid neutralization step may be produced in the catholyte compartment, recovered and re-used in future acid neutralization reactions or other chemical processes.

When an electrical potential is applied to the (4) anode, oxidation occurs. In one embodiment, the oxidation of a carboxylic acid or a carboxylate anion leads to decarboxylation, producing carbon dioxide and an alkyl radical. The radical can then combine with another alkyl radical to form alkyl-alkyl coupling products, following Kolbe electrolysis or it can react with other species present at the electrode's surface following non-Kolbe electrolysis. In another embodiment, when there is an electron donating group in the alpha position to the carboxyl group, the decarboxylation leads to the formation of $CO_2$ and a carbon cation from a two electron oxidation. Following its formation, the carbon cation can then participate in nucleophilic reactions instead of coupling reactions.

In one embodiment, the electrolytic cell may be operated in a continuous mode. In continuous mode, the cell is initially filled with anolyte solution and catholyte solution and then, during operation, additional solution is fed into the cell, and products, by-products, and/or diluted solutions are removed from the cell without ceasing operation of the cell. In another embodiment, the electrolytic cell is operated in batch mode. In batch mode, the anolyte solution and catholyte solution are fed initially into the cell and then the cell is operated until a desired concentration of the product is produced, then the cell is emptied and the products are collected. The cell is then refilled to start the process again. Also, in either method, the feeding of solution may be done using a premade solution or using components that form the solution in situ. It should be noted in both continuous and batch mode, the anolyte can be added to solution to maintain the alkali ion concentration at a certain level.

In one embodiment, the anolyte solution comprises of an IL electrolyte, and an alkali metal salt of a carboxylic acid. The choice of carboxylic acid is dependent on the desired product and can be chosen from any class of carboxylic acids. Some non-limiting examples are fatty acids, alkyl carboxylic acids, amino acids, aryl carboxylic acids, and di- and tri-carboxylic acids. The carboxylic acid can also have multiple substituents present, in addition to, the carboxylic group. These additional functional groups can be located at any carbon site of the carboxylic acid, and in some embodiments are located in the alpha position to the carboxylate carbon. Both electron donating and withdrawing substituent can be present on the carboxylic acid. Some non-limiting examples of electron donating substituents are hydroxyl, amine, amide, and ether groups. Some non-limiting examples of electron withdrawing substituents are halogens, nitriles, carbonyl, nitro, and nitride groups. The functional group present in the alpha position to the carboxylate will determine whether the decarboxylation will follow a one electron or two electron oxidation mechanism. In one embodiment, one electron oxidation will occur, favoring radical-radical coupling because there is no substituent present in the alpha position or the substituent is an electron withdrawing group. In another embodiment, the two electron oxidation is favored, because there is an electron donating group present in the alpha position to the carboxylate group.

In one embodiment, the first step is to convert the carboxylic acid ($RCO_2H$) into the corresponding alkali salt ($RCO_2M$) via acid neutralization. Where M is an alkali metal such as lithium, sodium or potassium: $RCO_2H$ is a carboxylic acid and R is a hydrocarbon having a $C_2$ to $C_{22}$ hydrocarbon chain and at least one hydrogen that has been substituted for a functional group containing oxygen. Some non-limiting examples of functional groups that can be present are hydroxyl, phenyl, esters, ethers, and ketones. In one embodiment, the carboxylic acid has other substituents which do not contain oxygen such as: halide, nitrile, amine, amide, and sulfide. In one embodiment, the carboxylic acid is obtained from biomass with the additional substituent already present. In another embodiment, the biomass derived carboxylic acid is first modified to include the additional functional groups.

The alkali carboxylate is added to a suitable IL electrolyte which is used as the anolyte solution. The anolyte solution may optionally include a supporting electrolyte if the conductivity of the alkali carboxylate is low and causes high solution resistance. The anolyte solution is fed either continuously or in batch mode into the electrochemical cell, such as the cell shown in the schematic of FIG. 1.

In one embodiment, when an (11) electrical potential is applied between the anode and cathode, the oxidation at the anode causes the decarboxylation of the carboxylate anion, leading to the formation of carbon dioxide, and radicals of (R.) according to the reaction below.

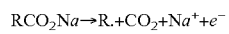
$$RCO_2Na \rightarrow R. + CO_2 + Na^+ + e^-$$

Once the radical is formed, it will react with other species at the electrode's surface, and if it reacts with another radical of the same carboxylate anion, it will form a homocoupling product as shown below.

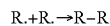
$$R. + R. \rightarrow R-R$$

This product can be in itself the chemical of interest, or it can be used as an intermediate precursor in the synthesis of the chemical of interest. For example, the function groups can be converted into double bonds and the diene can be used as monomers for the production of elastic material. If the radical combines with a radical of a different carboxylate anion, then a heterocoupling product will be formed and an unsymmetrical compound will be obtained. Again the heterocoupling product can be a chemical of interest or a precursor required to obtain a chemical of interest. In one embodiment, the decarboxylation will lead to a mixture of homocoupling and heterocoupling and thus provide a mixture of products. In one embodiment, this mixture is commercially viable, yet in another embodiment, the mixture will be further separated into a commercially viable product.

In one embodiment, the IL electrolyte is designed to facilitate the separation of the products from the reactants. One way this can be accomplished is by choosing the substituents on the cation that will force the products to separate from the IL electrolyte upon formation. Similarly, the IL electrolyte can be designed to have high solubility of the polar carboxylate reactants, and poor solubility of the products, such that when a non-polar solvent is mixed with the IL electrolyte either before or after the electrolysis, the products partition to the non-polar solvent. In another embodiment, the separation is facilitated by designing the IL electrolyte to have high thermal stability, thus product separation is accomplished because the cell is run at a temperature which the product is a gas and is easily separated from the IL electrolyte, Yet in another embodiment, the separation is facilitated by designing an IL electrolyte that has a high freezing point, such that upon cooling the ionic liquid crystallizes and the products remain a liquid and are separated by a simple method such as filtration.

Some advantages of using an IL electrolyte over the conventional polar organic electrolyte are: 1) the ionic liquid electrolyte can be custom designed to be chemically and electrochemical stable, 2) the electrolyte can be designed to permit high solubility of the carboxylate species, 3) the IL electrolyte can be designed to permit easy separation of the product and the reactant, 4) the IL electrolyte can be recycled and is environmentally friendly.

The following examples are given to illustrate various embodiments within the scope of the present invention.

EXAMPLES

Several examples will be given to demonstrate the technical feasibility of using custom ionic liquids as electrolytes to convert inexpensive carboxylic acids into high value compounds, using the electrochemical decarboxylati on process at low temperatures and pressures. The examples demonstrate the decarboxylation of sodium salts of carboxylic acids with a variety of functional groups, using electrolytic cells equipped with NaSelect® membranes manufactured by Ceramatec, Inc., SLC, Utah.

The examples disclosed herein, used an experimental setup which is schematically shown in FIG. 1. The cell employed for these experiments was a micro flow cell, allowing both the anolyte and catholyte to be pumped through the cell while minimizing the distance between the electrodes and the membrane. The membranes used in the examples consisted of 2.54 cm diameter NaSICON disks of about 1 mm thickness which were housed on scaffolds in the center of the cells. As the scaffold and membrane physically separate the anode and cathode compartments, there was a separate reservoir and temperature controlled hotplate for the anolyte and catholyte. This allowed the chemistry and conditions of each electrolyte to be optimized for the respective electrode reactions. A multiple-head peristaltic pump was used to pump both electrolytes into the electrolysis cell, and depending on the temperature of the electrolytes the tubing between the cell, pump, and reservoir was insulated.

The anolyte, which contains the sodium salt of the carboxylic acid, is made by dissolving at least 10% of the salt into a custom IL unless otherwise noted. This was conducted by preparing the sodium salt in a separate solution following conventional saponification reactions and then dissolving the prepared salt into the IL. For this method, a general saponification procedure was used during which the sodium carboxylate forms as the carboxylic acid is neutralized with sodium hydroxide. The details of the IL electrolyte preparation will be given in the different examples. The catholyte can be made from any solution containing sodium salts, and for the examples given herein an aqueous sodium hydroxide solution was used. To obtain low solution resistance, the temperature of the catholyte was increased to 50° C. to improve both the solubility and conductivity unless otherwise noted. The temperature of the IL anolyte was adjusted separately for each IL to minimize the viscosity.

In some embodiments, each M is sodium. In some embodiments, $R^1$ and $R^2$ are the same. In some embodiments, $R^1$ and $R^2$ are different.

Once the reservoirs reached the desired temperatures, a battery tester (Arbin MSTAT) was connected and a current density between 10 and 100 $mA/cm^2$ was applied. During the electrolysis the voltage and current were controlled and monitored using software that was supplied with the battery cycler (MITS Pro). The applied current density caused oxidation to occur at the anode (smooth platinum) and reduction to occur at the cathode (nickel), with each electrode having an area of 11 $cm^2$. As the power supply transports electrons from the anode to the cathode, a charge balance must be maintained across the cell by the diffusion of positively charge ions. Given the high selectivity of the NaSICON membrane for Na-ions, it is the only species that can provide this balance, thus a high concentration of the sodium salt was desired in the IL anolyte.

The method used to separate the product from the ionic liquid was determined by the ionic liquid and the particular product produced in the different examples. In all cases the reaction success was determined by measuring the product formation with GC analysis.

Example 1

A custom IL electrolyte was prepared for the purpose of being used in an electrochemical decarboxylation process to convert the sodium salt of a carboxylic acid into longer chain hydrocarbon dimers. The dimers produced can be used as a solvent or can be further processed for other applications such as fuels or lubricants. The IL electrolyte consisted of a 1-butyl-3-methylimidizolium cation and the anion of the IL electrolyte consisted of a carboxylate anion. The carboxylate anion was the same carboxylate being converted into the hydrocarbon dimer by the decarboxylation process.

The IL electrolyte was prepared by combining 1-butyl-3-methylimidizolium chloride and sodium octanoate. The sodium octanoate (96%, Alfa Aesar) and the 1-butyl-3-methylimidizolium chloride (95%, Aldrich) were dissolved in two separate flasks of methanol. The 1-butyl-3-methylimidizolium chloride and the sodium octanoate were measured out to contain an equivalent number of moles. These two methanol solutions were then mixed together at room temperature overnight to allow for complete ion exchange. This mixture was evaporated under vacuum until all the methanol was removed, leaving behind a mixture of salts. Acetonitrile was then added to the salts and the solution was mixed at room temperature overnight. The solids were filtered (Whatman grade 1 filter paper) off the acetonitrile solution and magnesium sulfate was added to the filtrate to remove residual water from the solution. The magnesium sulfate was removed from the acetonitrile filtrate by a second filtration step, after which the acetonitrile was removed under vacuum leaving the desired ionic liquid, 1-butyl-3-methylimidizolium octanoate.

Example 2

A custom IL electrolyte was prepared for the purpose of being used in an electrochemical decarboxylation process to convert the sodium salt of a carboxylic acid into longer chain hydrocarbon dimers. The dimers produced can be used as a solvent or can be further processed for other applications such as fuels or lubricants. The IL electrolyte was comprised of a 1-butylpyridinium cation and a carboxylate anion. The anion of the IL electrolyte consisted of the same carboxylate that was being converted to the hydrocarbon dimer by the decarboxylation process.

The IL electrolyte was prepared by combining 1-butylpyridinium chloride and sodium octanoate. The sodium octanoate and the 1-butylpyridinium chloride (98%, TCI) were added to a round-bottom flask and mixed until a homogenous mixture was obtained. The 1-butylpyridinium chloride and the sodium octanoate were measured out so there were 1.5 more moles of sodium octanoate than moles of the 1-butylpyridinium. Methanol was added and the solution was mixed at room temperature overnight under a $N_2$ atmosphere to permit complete ion exchange. This mixture was then evaporated under vacuum to completely remove the methanol, leaving behind a mixture of salts. Acetone was added to the salt solution and the solution was stirred at room temperature overnight under a $N_2$ atmosphere. The remaining solids were removed from the solution by filtration. The acetone was removed under vacuum producing the desired ionic liquid, 1-butylpyridinium octanoate.

Example 3

A custom IL electrolyte was prepared for the purpose of being used in an electrochemical decarboxylation process to convert the sodium salt of a carboxylic acid into longer chain hydrocarbon dimers. The dimers produced can be used as a solvent or can be further processed for other applications such as lubricants. The IL electrolyte was comprised of 1-butyl-1-methylpyrrolidinium cation and a carboxylate anion. The carboxylate anion is the same carboxylate being converted into the hydrocarbon dimer by the decarboxylation process.

The IL electrolyte was prepared by combining 1-butyl-1-methylpyrrolidinium chloride and sodium octanoate. The sodium octanoate and the 1-butyl-1-methylpyrrolidinium chloride (99%, Fluka) were mixed into a homogenous mixture using equimolar amounts of the two salts. To this, 100 mL acetonitrile and 20 mL isopropanol were added and the solution was mixed under a $N_2$ atmosphere to promote complete ion exchange. The remaining salts were filtered from the solution, and then the acetonitrile and isopropanol were removed under vacuum for several hours leaving behind the desired ionic liquid. This procedure was repeated with the solids removed by the filtration to ensure complete recovery of the 1-butyl-1-methylpyrrolidinium octanoate.

Example 4

A custom IL electrolyte was prepared for the purpose of being used in an electrochemical decarboxylation process to convert the sodium salt of a carboxylic acid into longer chain hydrocarbon dimers. The dimers produced can be used as a solvent or can be further processed for other applications such as fuels or lubricants. The IL electrolyte consisted of a triisobutyl(methyl)phosphonium cation and a carboxylate anion. The carboxylate anion is the carboxylate being converted to the hydrocarbon dimer by the decarboxylation process.

The IL electrolyte was prepared by combining triisobutyl(methyl)phosphonium tosylate and sodium octanoate. The sodium octanoate and the triisobutyl(methyl)phosphonium tosylate (CYTEC), were added to a round-bottom flask and mixed into an equimolar homogenous salt mixture. The salts were dissolved in 400 mL of methanol and mixed at 35° C. to allow for complete ion exchange. Following the ion exchange the methanol was removed under vacuum at 35° C. leaving behind a mixture of salts. The resulting salt mixture was then dissolved in diethyl ketone. The solution was stirred at 35° C. overnight to allow the IL to completely dissolve. The remaining solids were removed using filtration. The solvent was removed from the filtrate under vacuum producing the desired ionic liquid, triisobutyl(methyl)phosphonium octanoate.

Example 5

A custom IL electrolyte was prepared for the purpose of being used in an electrochemical decarboxylation process to convert the sodium salt of a carboxylic acid into longer chain hydrocarbon dimers. The dimers produced can be used as a solvent or can be further processed for other applications such as fuels and lubricants. The IL electrolyte was composed of a tetrabutylphosphonium cation and a carboxylate anion. The carboxylate anion was the same anion that was being converted into the hydrocarbon dimer by the decarboxylation process.

The IL electrolyte was prepared by reacting tetrabutylphosphonium hydroxide and octanoic acid. The octanoic acid (98%, Sigma Aldrich) and the tetrabutylphosphonium hydroxide (40% in $H_2O$, Aldrich) were mixed together to have equimolar amounts of both salts. These were permitted to mix at room temperature until complete neutralization of the acid and base was achieved. The water was then removed from the solution under vacuum preparing a tetrabutylphosphonium octanoate IL. An additional 3% by weight of sodium octanoate was then dissolved into the prepared phosphonium octanoate ionic liquid to prepare the electrolyte.

Another route to prepare the tetrabutylphosphonium octanoate consisted of combining tetrabutylphosphonium chloride and sodium octanoate. Equimolar amounts of tetrabutylphosphonium chloride (CYTEC) and sodium octanoate were combined in a flask under a nitrogen atmosphere. To this, 400 g of methanol was added, and the solution was stirred at 50° C. until complete ion exchange had occurred. The methanol was removed under vacuum, leaving a mixture of salts behind, which were dried overnight under $N_2$. 215 g of acetone was added to the salt mixture which dissolved the IL but not the sodium chloride. After removing the sodium chloride with filtration, the filtrate was evaporated under vacuum, giving the final product of tetrabutylphosphonium octanoate.

Example 6

A custom IL electrolyte was prepared and used in an electrochemical decarboxylation process to convert the sodium salt of a carboxylic acid with a hydroxyl group into a hydrocarbon diol. The diol produced can be used as a solvent or it can be further converted into a diene. The IL electrolyte was composed of a tetradecyl(trihexyl)phosphonium cation and a carboxylate anion. The carboxylate of the IL electrolyte is the same carboxylate being converted into the diol by the decarboxylation process. An aqueous solution containing 10% by weight sodium hydroxide was used as the catholyte.

The IL electrolyte was prepared by modifying tetradecyl(trihexyl)phosphonium chloride (CYTEC). This was performed by mixing 100 ml of the phosphonium chloride ionic liquid with a 100 ml of aqueous sodium lactate (60% in $H_2O$, Sigma). The aqueous sodium lactate was prepared to have an equivalent number of moles of lactate anions as the number of moles of chloride present in the ionic liquid. These were mixed at 50° C. for 12 h, after which the mixture was transferred to a separatory funnel. The water layer was removed from the newly formed ionic liquid, and the ionic liquid was washed three times with DI water. Following the third wash the ionic liquid was dried with anhydrous magnesium sulfate, which was filtered off the prepared ionic liquid. To the prepared IL, 20% by weight sodium lactate was dissolved to prepare the IL electrolyte.

The electrolysis of the ionic liquid was conducted in batch mode, during which the anolyte and catholyte were cycled through the corresponding anode and cathode compartments of the cell. The cell was operated until enough charge passed to theoretically convert 80% of the added sodium lactate. During the electrolysis the temperatures of the electrolytes were maintained at 50° C., and a current density of 9 mA $cm^{-2}$ was employed.

The reactions that occurred during the electrolysis in the anode and cathode compartment are shown below.

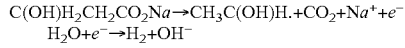

$H_2O + e^- \rightarrow H_2 + OH^-$

Figure 2:
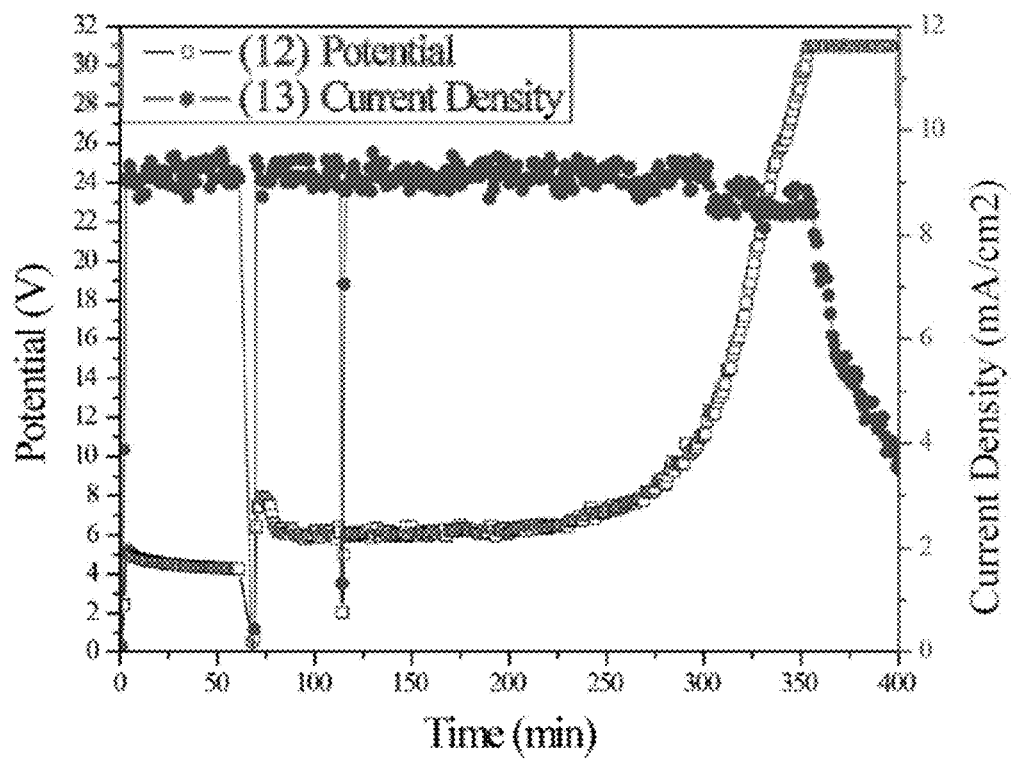
FIG. 2 is a plot of the cell potential and current density of the electrochemical decarboxylation of sodium lactate in tetradecyl(trihexyl)phosphonium lactate.

The decarboxylation occurring in the anode compartment produced $CO_2$ which was bubbled through a calcium hydroxide solution forming calcium carbonate which was then analyzed using TGA. FIG. 2 contains the time transients of the (12) potential and (13) current density for the electrolysis. The potential started just below 7 V and increased to 31 V in 6 h causing decarboxylation to occur. The conditions used in this example promoted radical-radical coupling and produced 2,3-butanediol according to reaction below.

Figure 3:
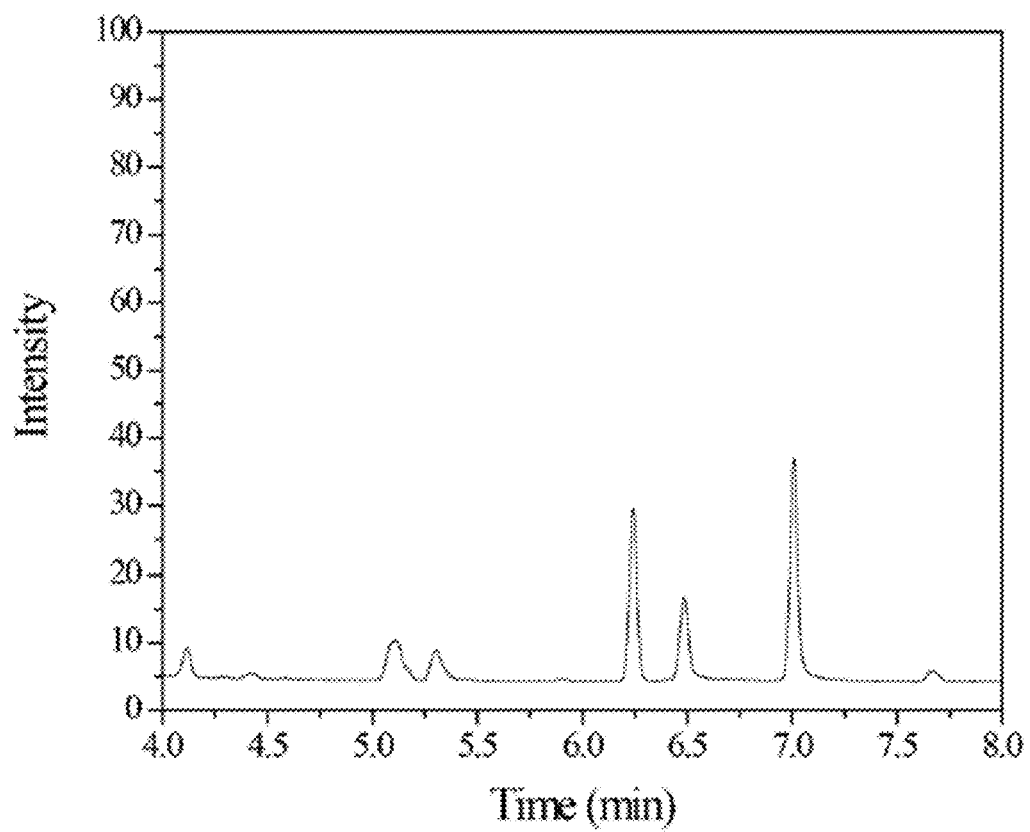
FIG. 3 shows a gas chromatogram of the products obtained from the electrochemical decarboxylation of sodium lactate in tetradecyl(trihexyl)phosphonium lactate.

After the electrolysis was completed the product was distilled from the IL electrolyte under vacuum and the analysis was conducted using a gas chromatograph (GC) equipped with a 30 m capillary column (0.53 mm i.d., GS-Alumina column, Agilent), a flame ionize detector (FID) and using helium as the carrier gas. The injector and detector temperature were 120 and 220° C., respectively and the chromatograms were conducted isothermally at 125° C., or starting at 125° C. and increasing the temperature at a rate of 10° C. $min^{-1}$ to 200° C., and then holding this temperature for 10 min. The GC of the product is shown in FIG. 3 with the two peaks at 6.5 and 7.1 min being the elution of the 2,3-butanediol isomers.

Example 7

An IL customized was used in an electrochemical decarboxylation process to convert the sodium salt of a long chain carboxylic acid with a double bond into a longer chain olefin with two double bonds. The IL electrolyte consisted of the same cation used in EXAMPLE 6, and the anion of the IL electrolyte consisted of the oleate anion that was being converted into the long chain olefin by the decarboxylation process. An aqueous solution containing 10% by weight sodium hydroxide was used as the catholyte.

The II electrolyte was prepared by modifying tetradecyl (trihexyl) phosphonium chloride. This was performed by mixing 100 ml of the phosphonium chloride ionic liquid with a 100 ml of aqueous sodium oleate (97%, TCI). The aqueous sodium oleate was prepared to have an equivalent number of moles of oleate anions to the number of moles of chloride present in the ionic liquid. These were mixed at 50° C. for 12 h, after which the mixture was transferred to a separatory funnel. The water layer was removed from the newly formed ionic liquid, and the ionic liquid was washed three times with DI water. Following the third wash the ionic liquid was dried with anhydrous magnesium sulfate. 20% by weight sodium oleate was dissolved in the prepared phosphonium oleate ionic liquid.

The electrolysis was conducted in batch mode, during which the anolyte and catholyte were cycled through the corresponding anode and cathode compartments of the cell. The cell was operated until enough charge passed to theoretically convert 80% of the added sodium salt. During the electrolysis the temperatures of the electrolytes were maintained at 50° C., and a current density of 45 mA $cm^{-2}$ was employed.

The reactions that occurred during the electrolysis in the anode and cathode compartment are shown below.

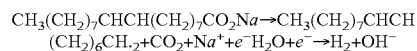

$(CH_2)_6CH_2 + CO_2 + Na^+ + e^-$ $H_2O + e^- \rightarrow H_2 + OH^-$

Figure 4:
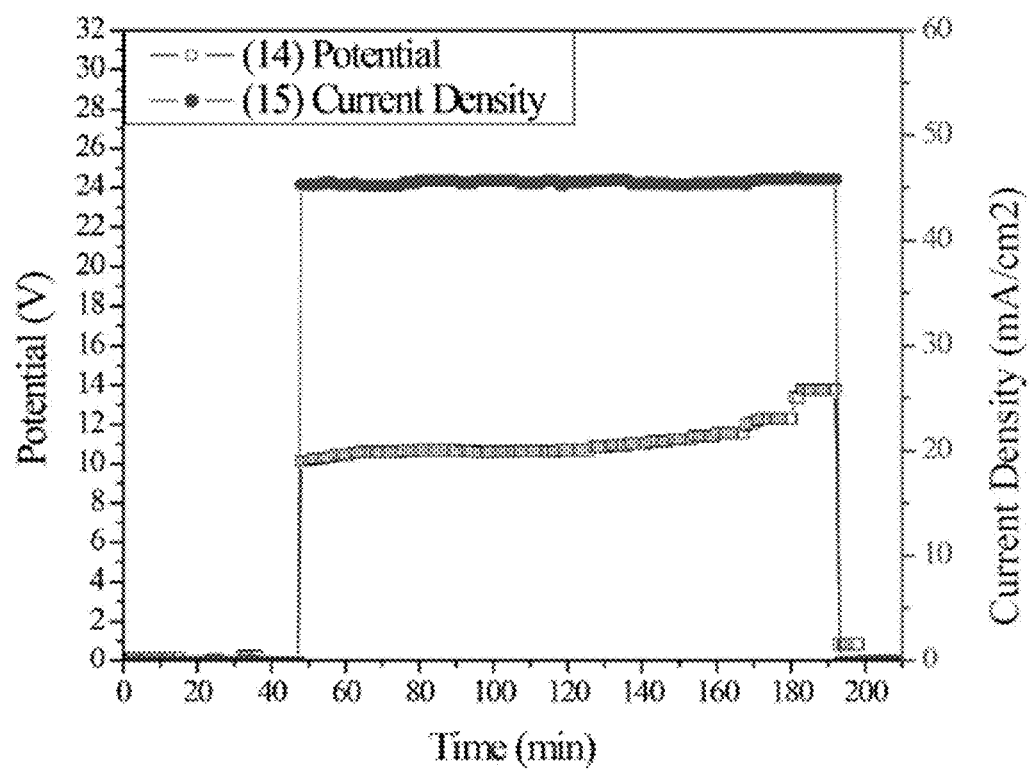
FIG. 4 is a plot of the cell potential and current density of the electrochemical decarboxylation of sodium oleate in tetradecyl(trihexyl)phosphonium oleate.

The decarboxylation occurring in the anode compartment produced $CO_2$ which was bubbled through a calcium hydroxide solution forming calcium carbonate which was then analyzed using TGA. FIG. 4 contains time transients of the (14) potential and (15) current density for the electrolysis. The potential started just below 11 V and increased to 14 V in 2 h causing decarboxylation to occur. The conditions used in this example promoted radical-radical coupling and produced $C_{34}H_{66}$ according to reaction below.

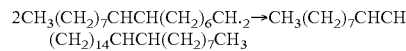

Figure 5:
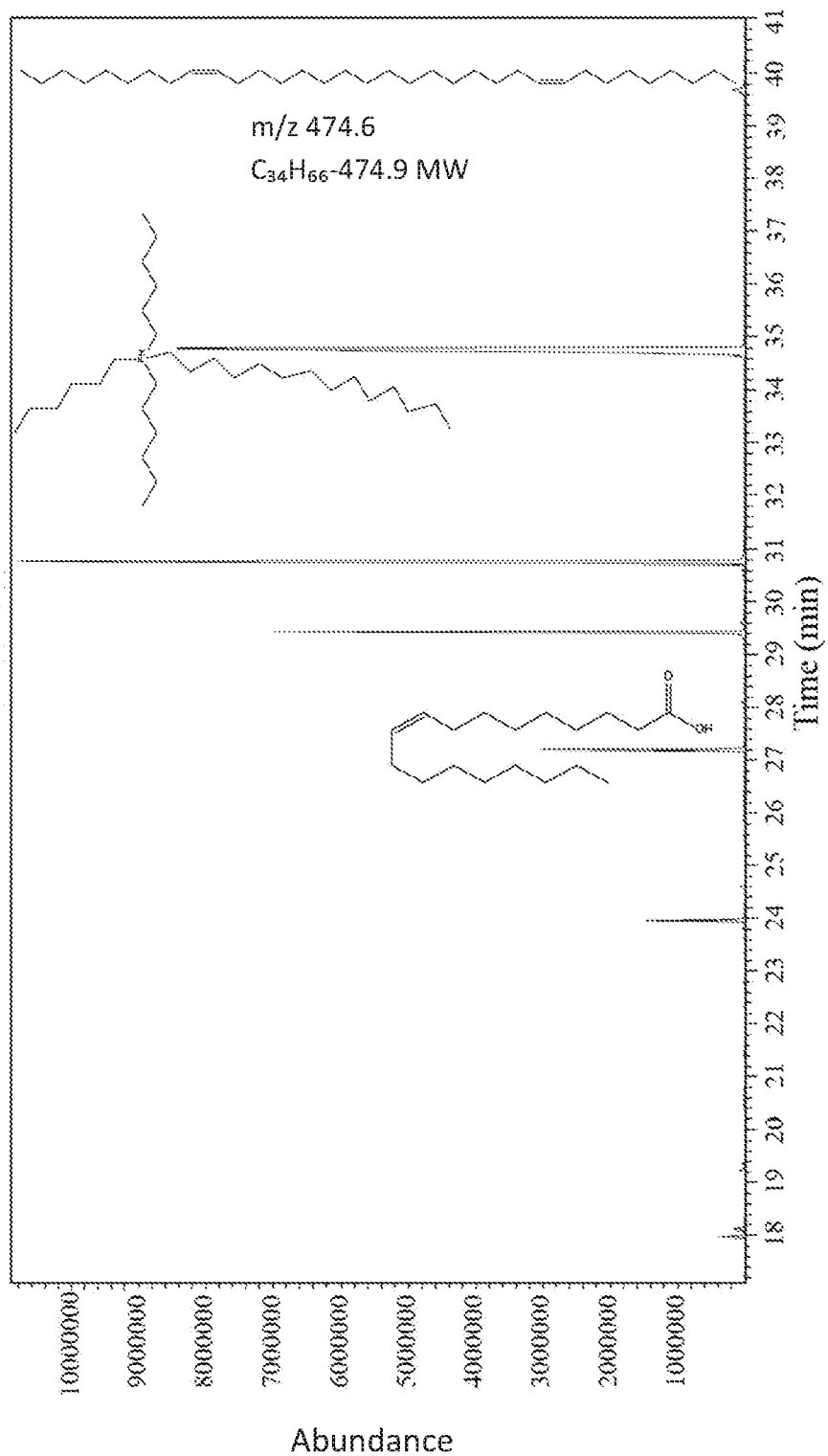
FIG. 5 shows a gas chromatogram of the products obtained from the electrochemical decarboxylation of sodium oleate in tetradecyl(trihexyl)phosphonium oleate.

After the electrolysis was completed the product was isolated from the IL electrolyte by mixing it with water and dodecane. After mixing, the mixture was placed in a separatory funnel and the dodecane layer was separated and analyzed with GC and MS. The GC-MS analysis was conducted using a 60 m column with a non-polar dimethylpolysiloxane phase which can handle a temperature range between −60-325° C., A temperature program was used that started at 35° C. and rose to 310° C. at 10°/min and then held this temperature for 35 min. The mass spec range used to analyze the data was 29 to 550 m/z. The identity of the peaks eluded in the GC shown in FIG. 5, were determined using mass spectroscopy, with the results of some of the peaks shown on the Figure. FIG. 5 shows the presence of the $C_{34}H_{66}$ product which eluded at 39.6 min, along with the presence of the oleic acid and the phosphonium cation.

Example 8

A custom IL electrolyte was prepared for the purpose of being used in an electrochemical decarboxylation process to convert the sodium salt of a carboxylic acid into longer chain hydrocarbon dimers. The dimers produced can be used as a solvent or can be further processed for other applications such as lubricants. The IL electrolyte was composed of a tributyloctylphosphonium cation and a carboxylate anion. The carboxylate anion was the same anion that was being converted into the hydrocarbon dimer by the decarboxylation process.

The IL electrolyte was prepared by combining tributyloctylphosphonium chloride and sodium octanoate. Equimolar amounts of tributyloctylphosphonium chloride (CYTEC) and sodium octanoate were combined in a flask. To this, 232 g DI water was added and the solution stirred at 50° C. overnight until complete ion exchange had occurred. The solution was transferred to a separatory funnel and washed by removing portions of the aqueous layer and replacing the removed portions with fresh DI water. After the final wash with DI water the ionic liquid was dried under vacuum with mild heat. The prepared ionic liquid was then washed two times with 3.5% by weight aqueous sodium octanoate one time with 10% by weight aqueous sodium octanoate, and one time with DI water. Before separating the last wash of DI water 1% aqueous silver nitrate was added, causing any remaining chloride to precipitate out as silver chloride. The resulting solution was centrifuged, decanted and filtered to remove precipitates. Drying the resulting IL layer under vacuum gave the final tributyloctylphosphonium octanoate electrolyte.

The electrolysis of the ionic liquid was conducted in batch mode, during which the anolyte and catholyte were cycled through the corresponding anode and cathode compartments of the cell. The cell was operated at stepwise current between 3.1 mA cm$^{-2}$ current density and 25 mA cm$^{-2}$ for 15 minutes. During the electrolysis the temperatures of the electrolytes were maintained at 120° C. for the anolyte and 70° C., for the catholyte. The reactions that occurred during the electrolysis in the anode and cathode compartment are shown below.

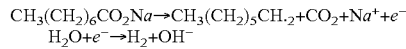

Figure 6:
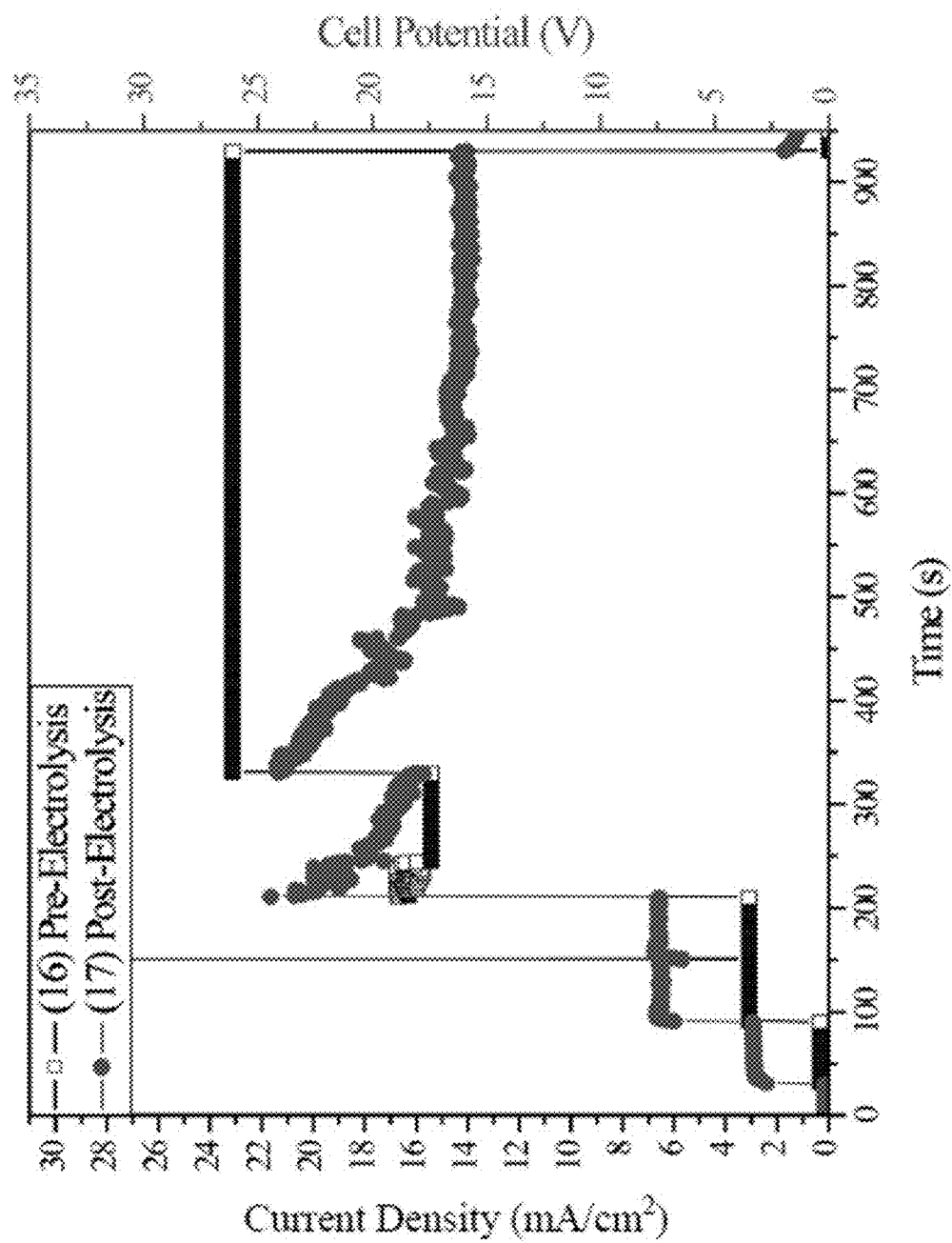
FIG. 6 is a plot of the cell potential and current density of the electrochemical decarboxylation of sodium octanoate in tribututyloctylphosphonium octanoate.

The decarboxylation occurring in the anode compartment produced $CO_2$. FIG. 6 contains the time transients of the (16) potential and (17) current density for the electrolysis. The potential started just below 3.3 V at 3.1 mA cm$^{-2}$ current density and increased to an average of 17.6 V at 23.4 mA cm$^2$ current density in 15 minutes causing decarboxylation to occur. The conditions used in this example promoted radical-radical coupling and produced tetradecane according to reaction below.

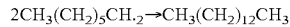

Figure 7:
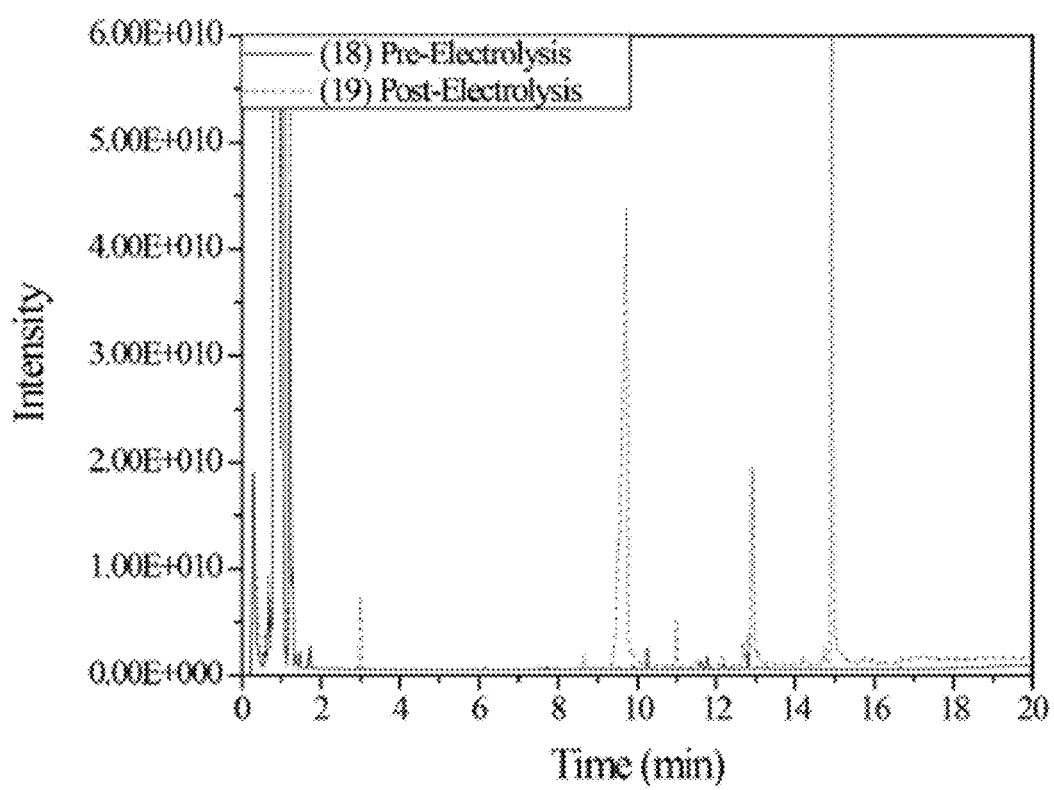
FIG. 7 shows a gas chromatogram of the products obtained from the electrochemical decarboxylation of sodium octanoate in tribututyloctylphosphonium octanoate.

After the electrolysis was completed the product was extracted from the IL electrolyte using hexane to perform a liquid/liquid extraction. The analysis was conducted using a GC with MS as the detector, equipped with a 30 m capillary column (0.32 mm i.d., 100% polymethylsiloxane column, Bruker), and using helium as the carrier gas. The injector temperature was 300° C. and the chromatograms were conducted isothermally at 40° C., or starting at 40° C. for two minutes and increasing the temperature at a rate of 10° C. min$^{-1}$ to 300° C., and then holding this temperature for 5 min. The GC of the product is shown in FIG. 7 with the peak at 11 min being the elution of the tetradecane.

Example 9

A custom IL electrolyte was prepared for use in an electrochemical decarboxylation process to convert the sodium salt of a carboxylic acid into longer chain hydrocarbon dimers. The dimers produced can be used as a solvent or can be further processed for other applications such as fuels or lubricants. The IL electrolyte consisted of a tetramethylammonium cation and a carboxylate anion. The carboxylate anion was the same carboxylate that was being decarboxylated to form the hydrocarbon dimer.

The IL electrolyte was prepared by reacting tetramethylammonium hydroxide and octanoic acid. The octanoic acid and the tetramethyl ammonium hydroxide (25% in $H_2O$, Sigma Aldrich) were slowly mixed together. The tetramethylammonium hydroxide was measured out to contain an equivalent number of moles to the octanoic acid. These were mixed at room temperature to allow for complete neutralization of the acid and base. This mixture was evaporated at 40° C. under vacuum until all the water had been removed. Following the evaporation of water, the final product of tetramethylammonium octanoate was obtained. This was found to melt at 100° C. and be stable to the addition of additional sodium octanoate needed to be used as an electrolyte.

Example 10

A custom IL electrolyte was prepared for use in an electrochemical decarboxylation process to convert the sodium salt of a carboxylic acid into longer chain hydrocarbon dimers. The dimers produced can be used as a solvent or can be further processed for other applications such as fuels or lubricants. The IL electrolyte consisted of a benzyltrimethylammonium cation and a carboxylate anion. The carboxylate anion of the custom IL electrolyte is the same carboxylate anion being converted into the hydrocarbon dimer by the decarboxylati on process.

The IL electrolyte was prepared by reacting benzyltrimethylammonium hydroxide and octanoic acid. The octanoic acid and the benzyltrimethylammonium hydroxide (40% in $H_2O$, TCI) were slowly mixed together. The benzyltrimethylammonium hydroxide was measured out to contain an equivalent number of moles as the octanoic acid. These were mixed at room temperature to allow complete neutralization of the acid and base. This mixture was evaporated at 40° C. under vacuum until all water was removed producing the benzyltrimethylammonium octanoate IL.

Example 11

A custom IL electrolyte was prepared for the purpose of being used in an electrochemical decarboxylation process to convert the sodium salt of a carboxylic acid into longer chain hydrocarbon dimers. The dimers produced can be used as a solvent or can be further processed for other applications such as fuels or lubricants. The IL electrolyte consisted of a tetrabutylammonium cation and a carboxylate anion. The anion of the IL electrolyte is the same carboxylate being converted into the hydrocarbon dimer by the decarboxylation process.

The II electrolyte was prepared by reacting tetrabutylammonium hydroxide and octanoic acid. The octanoic acid and the tetrabutylammonium hydroxide (40% in $H_2O$, Fluka) were slowly mixed together. The tetrabutyl-ammonium hydroxide was measured out to contain an equivalent number of moles to the octanoic acid. These were mixed at room temperature for several minutes to allow for complete neutralization of the acid and base. This mixture was evaporated at 40° C. under vacuum for several hours until all the water had been removed. After the removal of water, 3% by weight sodium octanoate was dissolved in the room temperature ionic liquid to make the electrolyte solution that was used as the anolyte in the electrolysis.

Another method used to prepare the tetrabutylammonium octanoate ionic liquid was performed using tetrabutylammonium chloride (97%, Aldrich) and sodium octanoate. Equimolar amounts of tetrabutylammonium chloride and sodium octanoate were combined in a flask. To this, 300 g of methanol was added, and the solution was allowed to stir for several hours during which time ion exchange between the chloride and octanoate occurred. The solution was maintained in a $N_2$ atmosphere for the duration of the preparation process. Following the ion exchange, the methanol was evaporated under vacuum, causing the compounds to recrystallize. 360 g of dichloromethane was added to the resulting salts, which dissolved the newly formed IL ions, but not the sodium chloride formed by the ion exchange. The solids were filtered from the solution, and the filtrate was evaporated under vacuum. The solids from the filtration were redissolved in dichloromethane and the separation procedure was repeated two more times to extract as much of the IL as possible.

The electrolysis of tetrabutylammonium octanoate was conducted in batch mode, during which the anolyte and catholyte were placed in separate compartments of a reactor with a NaSICON membrane separating the compartments. An aqueous solution containing 10% by weight sodium hydroxide was used as the catholyte and both the anolyte and catholyte were maintained at 40° C. The cell was operated for 28 h at a constant potential of 12.0 V which produced an average current density of 9.5 mA cm$^{-2}$.

The reactions that occurred during the electrolysis in the anode and cathode compartment are shown below.

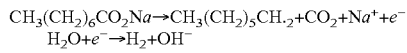

The conditions used in this example promoted radical-radical coupling and produced $C_{14}H_{30}$ according to reaction below.

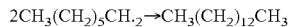

Figure 8:
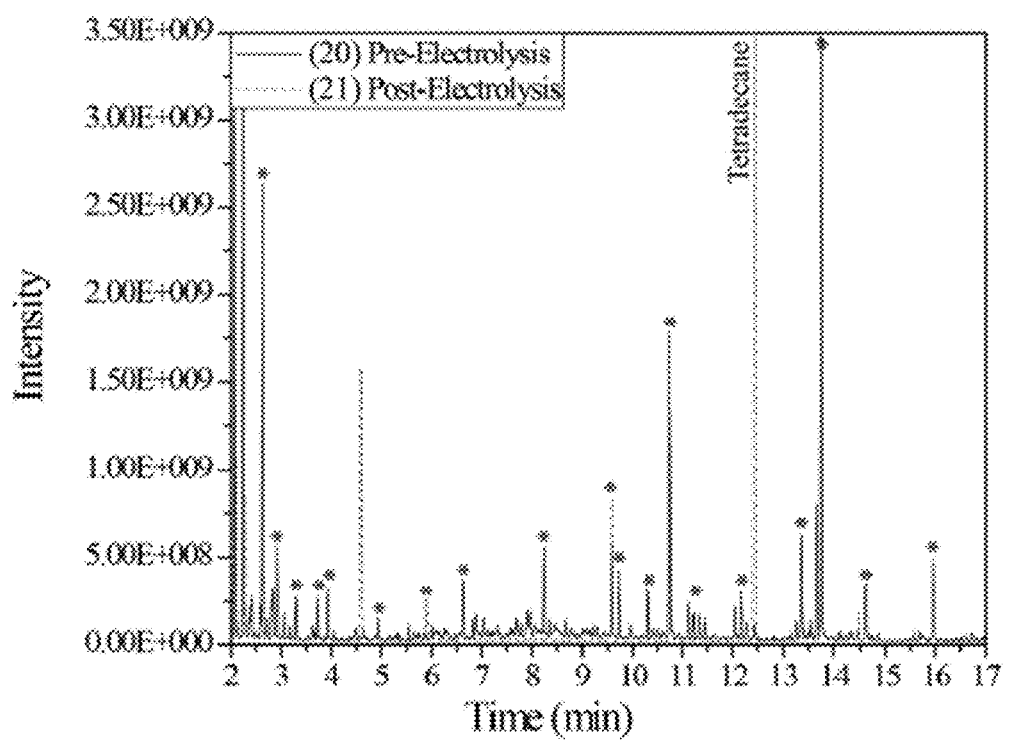
FIG. 8 shows the gas chromatograms of the pre- and post-electrolysis from the electrochemical decarboxylation of sodium oleate in tetrabutylammonium octanoate.

After the electrolysis was completed the product was isolated from the IL electrolyte using hexane to perform a liquid-liquid extraction. The hexane layer was analyzed with GC-MS, which was used to identify the peaks eluded in the GCs shown in FIG. 8. Peaks that are similar in the pre- (20) and post-electrolysis (21) are marked with an asterisk, and the post electrolysis GC (21) shows the presence of the $C_{14}H_{30}$ product which eluded at 12.5 min.

What is claimed is:

1. A method of making a compound of formula $R^1$-$R^2$, comprising:
    providing an electrolytic cell, comprising:
        an anode compartment comprising an ionic liquid electrolyte;
        a cathode compartment comprising aqueous sodium hydroxide;
        an alkali ion selective membrane separating the anode compartment and the cathode compartment;
        an anode in communication with the ionic liquid electrolyte;
        a cathode in communication with the aqueous sodium hydroxide;
        a power supply; and
    applying an electric current to the ionic liquid electrolyte;
    wherein the ionic liquid comprises compounds having formulas $R^1COOM$ and $R^2COOM$ and wherein each of $R^1$ and $R^2$ is independently selected from unsubstituted and substituted alkyl, unsubstituted and substituted cycloalkyl, unsubstituted and substituted heterocyclyl, substituted and unsubstituted alkenyl, substituted and unsubstituted alkynyl, substituted and unsubstituted aryl, and substituted and unsubstituted heteroaryl;
    wherein each M is independently an alkali metal;
    wherein the power supply provides an electric potential between the anode and the cathode; and
    wherein the electric potential provided by the power supply oxidizes the anode and decarboxylates the compounds of formulas $R^1COOM$ and $R^2COOM$ to form a decarboxylated radical of $R^1$ and $R^2$, which further undergo radical-radical coupling to provide a compound of formula $R^1$-$R^2$;
    wherein the ionic liquid has the formula $[(R')(R'')(R''')(R'''')X]$;
    wherein X is selected from substituted or unsubstituted pyridinium, substituted or unsubstituted pyridazinium, substituted or unsubstituted pyrimidinium, substituted or unsubstituted pyrazinum, substituted or unsubstituted pyrrolidinium, substituted or unsubstituted imidazolium, substituted or unsubstituted pyrazolium, substituted or unsubstituted thiazolium, substituted or unsubstituted oxazolium, substituted or unsubstituted triazolium, phosphonium, and ammonium; and
    wherein each of R', R'', R''', and R'''' is the same and is selected from fluoro, phosphinates, alkylphosphinates, alkylthiophosphinates, sulfates, sulphonates, amides, tosylates, aluminates, borates, arenates, cuprates, nitrates, carboxylates, hydrogen, unsubstituted and substituted alkyl, unsubstituted and substituted cycloalkyl, unsubstituted and substituted heterocyclyl, substituted and unsubstituted alkenyl, substituted and unsubstituted alkynyl, substituted and unsubstituted aryl, and substituted and unsubstituted heteroaryl,
    provided that when X is ammonium or phosphonium, then each of R', R'', R''', and R'''' may also independently be hydrogen.

2. The method of claim 1, wherein substitutions on substituted alkyl, cycloalkyl, heterocyclyl, alkenyl, alkynyl, aryl, and heteroaryl are selected from halogen, unsubstituted $C_{1-8}$ alkyl, —CN, —NO$_2$, =O, —C(O)R$^A$, —CO$_2$R$^A$, —C(O)NR$^A$R$^B$, —OR$^A$, —OC(O)R$^A$, —OC(O)NR$^A$R$^B$, —NR$^C$C(O)R$^A$, —NR$^C$(O)NR$^A$R$^B$, —NR$^A$R$^B$, —NR$^C$CO$_2$R$^A$, —NR$^C$S(O)$_2$R$^A$, —SR$^A$, —S(O)R$^A$, —S(O)$_2$R$^A$, —S(O)$_2$NR$^A$R$^B$;
    wherein each of R$^A$, R$^B$, and R$^C$, when present, is independently selected from the group consisting of: —H, unsubstituted $C_{1-8}$ alkyl, unsubstituted $C_{2-8}$ alkenyl, and unsubstituted $C_{2-8}$ alkynyl.

3. The method of claim 1, wherein substitutions on substituted alkyl, cycloalkyl, heterocyclyl, alkenyl, alkynyl, aryl, and heteroaryl are located geminal to —COOM.

4. The method of claim 1, further comprising contacting a compound of formula $R^1COOH$ with an alkaline hydroxide of formula MOH to provide a compound of formula $R^1COOM$.

5. The method of claim 1, further comprising contacting a compound of formula $R^2COOH$ with an alkaline hydroxide of formula MOH to provide a compound of formula $R^2COOM$.

6. The method of claim 1, further comprising heating the ionic liquid.

7. The method of claim 1, wherein each M is sodium.

8. The method of claim 1, wherein $R^1$ and $R^2$ are the same or different.

9. The method of claim 1, further comprising contacting the ionic liquid with an organic solvent.

10. The method of claim 1, further comprising contacting the ionic liquid with a supporting electrolyte.

11. The method of claim 10, wherein the supporting electrolyte is selected from alkali metal hydroxide, alkali metal salts, tetrafluoroborate, tetramethylammonium hexafluorophosphate, tetrabutylammonium tetrafluoroborate, tetramethylammonium perchlorate, and tetraethylammonium perchlorate.

12. The method of claim 1, wherein the alkali ion selective membrane comprises at least one of LISICON and NASICON.

13. A method of making a compound of formula $R^1\text{-}R^2$, comprising:
providing an electrolytic cell, comprising:
an anode compartment comprising an ionic liquid electrolyte;
a cathode compartment comprising aqueous sodium hydroxide;
an alkali ion selective membrane separating the anode compartment and the cathode compartment;
an anode in communication with the ionic liquid electrolyte;
a cathode in communication with the aqueous sodium hydroxide;
a power supply; and
applying an electric current to the ionic liquid electrolyte;
wherein the ionic liquid comprises compounds having formulas $R^1COOM$ and $R^2COOM$ and wherein each of $R^1$ and $R^2$ is independently selected from unsubstituted and substituted alkyl, unsubstituted and substituted cycloalkyl, unsubstituted and substituted heterocyclyl, substituted and unsubstituted alkenyl, substituted and unsubstituted alkynyl, substituted and unsubstituted aryl, and substituted and unsubstituted heteroaryl;
wherein each M is independently an alkali metal;
wherein the power supply provides an electric potential between the anode and the cathode; and
wherein the electric potential provided by the power supply oxidizes the anode and decarboxylates the compounds of formulas $R^1COOM$ and $R^2COOM$ to form a decarboxylated radical of $R^1$ and $R^2$, which further undergo radical-radical coupling to provide a compound of formula $R^1\text{-}R^2$;
wherein the ionic liquid has the formula [(R')(R'')(R''')(R'''')X];
wherein X is selected from substituted or unsubstituted pyridinium, substituted or unsubstituted pyridazinium, substituted or unsubstituted pyrimidinium, substituted or unsubstituted pyrazinum, substituted or unsubstituted pyrrolidinium, substituted or unsubstituted imidazolium, substituted or unsubstituted pyrazolium, substituted or unsubstituted thiazolium, substituted or unsubstituted oxazolium, substituted or unsubstituted triazolium, phosphonium, and ammonium; and
wherein at least one of R', R'', R''', and R'''' is different from the others and each of R', R'', R''', and R'''' is independently selected from fluoro, phosphinates, alkylphosphinates, alkylthiophosphinates, sulfates, sulphonates, amides, tosylates, aluminates, borates, arenates, cuprates, nitrates, carboxylates, hydrogen, unsubstituted and substituted alkyl, unsubstituted and substituted cycloalkyl, unsubstituted and substituted heterocyclyl, substituted and unsubstituted alkenyl, substituted and unsubstituted alkynyl, substituted and unsubstituted aryl, and substituted and unsubstituted heteroaryl,
provided that when X is ammonium or phosphonium, then each of R', R'', R''', and R'''' may also independently be hydrogen.

14. The method of claim 13, wherein substitutions on substituted alkyl, cycloalkyl, heterocyclyl, alkenyl, alkynyl, aryl, and heteroaryl are selected from halogen, unsubstituted $C_{1-8}$ alkyl, —CN, —$NO_2$, =O, —C(O)$R^A$, —$CO_2R^A$, —C(O)$NR^AR^B$, —$OR^A$, —OC(O)$R^A$, —OC(O)$NR^AR^B$, —$NR^C(O)R^A$, —$NR^C(O)NR^AR^B$, —$NR^AR^B$, —$NR^CCO_2R^A$, —$NR^CS(O)_2R^A$, —$SR^A$, —S(O)$R^A$, —$S(O)_2R^A$, —$S(O)_2NR^AR^B$;
wherein each of $R^A$, $R^B$, and $R^C$, when present, is independently selected from the group consisting of: —H, unsubstituted $C_{1-8}$alkyl, unsubstituted $C_{2-8}$ alkenyl, and unsubstituted $C_{2-8}$ alkynyl.

15. The method of claim 13, wherein substitutions on substituted alkyl, cycloalkyl, heterocyclyl, alkenyl, alkynyl, aryl, and heteroaryl are located geminal to —COOM.

16. The method of claim 13, further comprising contacting a compound of formula $R^1COOH$ with an alkaline hydroxide of formula MOH to provide a compound of formula $R^1COOM$.

17. The method of claim 13, further comprising contacting a compound of formula $R^2COOH$ with an alkaline hydroxide of formula MOH to provide a compound of formula $R^2COOM$.

18. The method of claim 13, further comprising heating the ionic liquid.

19. The method of claim 13, wherein each M is sodium.

20. The method of claim 13, wherein $R^1$ and $R^2$ are the same or different.

21. The method of claim 13, further comprising contacting the ionic liquid with an organic solvent.

22. The method of claim 13, further comprising contacting the ionic liquid with a supporting electrolyte.

23. The method of claim 22, wherein the supporting electrolyte is selected from alkali metal hydroxide, alkali metal salts, tetrafluoroborate, tetramethylammonium hexafluorophosphate, tetrabutylammonium tetrafluoroborate, tetramethylammonium perchlorate, and tetraethylammonium perchlorate.

24. The method of claim 13, wherein the alkali ion selective membrane comprises at least one of LISICON and NASICON.

* * * * *